United States Patent
Charron et al.

(10) Patent No.: US 11,160,614 B2
(45) Date of Patent: Nov. 2, 2021

(54) SURGICAL IMAGING SENSOR AND DISPLAY UNIT, AND SURGICAL NAVIGATION SYSTEM ASSOCIATED THEREWITH

(71) Applicant: SYNAPTIVE MEDICAL INC., Toronto (CA)

(72) Inventors: Luc Gilles Charron, Toronto (CA); Michael Frank Gunter Wood, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 498 days.

(21) Appl. No.: 16/154,158

(22) Filed: Oct. 8, 2018

(65) Prior Publication Data
US 2019/0117318 A1 Apr. 25, 2019

(51) Int. Cl.
*A61B 34/20* (2016.01)
*A61B 90/00* (2016.01)
(Continued)

(52) U.S. Cl.
CPC .......... *A61B 34/20* (2016.02); *A61B 5/0059* (2013.01); *A61B 5/0077* (2013.01); *A61B 5/704* (2013.01); *A61B 5/743* (2013.01); *A61B 34/10* (2016.02); *A61B 34/30* (2016.02); *A61B 90/20* (2016.02); *A61B 90/361* (2016.02); *A61B 90/37* (2016.02); *A61B 5/1127* (2013.01); *A61B 34/70* (2016.02); *A61B 2034/2055* (2016.02); *A61B 2034/305* (2016.02); *A61B 2090/371* (2016.02); *A61B 2090/372* (2016.02); *A61B 2090/373* (2016.02); *A61B 2090/3735* (2016.02);
(Continued)

(58) Field of Classification Search
CPC . A61B 34/20; A61B 34/30; A61B 2034/2055; A61B 5/0077; A61B 90/37; A61B 2090/372; A61B 2090/373
See application file for complete search history.

(56) References Cited

U.S. PATENT DOCUMENTS

| | | | | |
|---|---|---|---|---|
| 7,203,277 B2 * | 4/2007 | Birkenbach | ............ | A61B 6/032 378/205 |
| 7,463,823 B2 * | 12/2008 | Birkenbach | ............ | G03B 41/00 348/42 |

(Continued)

FOREIGN PATENT DOCUMENTS

| | | | | |
|---|---|---|---|---|
| WO | WO-2016084093 A1 * | 6/2016 | ............ | A61B 5/055 |
| WO | 2018/049196 A1 | 3/2018 | | |

OTHER PUBLICATIONS

Search Report issued by the Intellectual Property Office of the United Kingdom in relation to corresponding GB Application No. GB1817323.7 dated Apr. 10, 2019, 4 pgs.

(Continued)

*Primary Examiner* — Boniface N Nganga

(57) ABSTRACT

Described are various embodiments of a mobile surgical imaging sensor and display unit, and surgical navigation system associated therewith, in which the mobile unit may be disposed to provide line-of-sight or near line-of-sight imaging and display capabilities to an operator thereof during a surgical procedure, while a position and/or orientation of the mobile unit is tracked relative to a surgical site to associate a surgical site location with images captured and rendered by the mobile unit.

20 Claims, 11 Drawing Sheets

(51) Int. Cl.
- *A61B 34/30* (2016.01)
- *A61B 5/00* (2006.01)
- *A61B 90/20* (2016.01)
- *A61B 34/10* (2016.01)
- *H04N 13/363* (2018.01)
- *A61B 34/00* (2016.01)
- *H04N 13/398* (2018.01)
- *A61B 5/11* (2006.01)

(52) U.S. Cl.
CPC ....... *A61B 2505/05* (2013.01); *A61B 2576/00* (2013.01); *H04N 13/363* (2018.05); *H04N 13/398* (2018.05)

(56) References Cited

U.S. PATENT DOCUMENTS

| | | | |
|---|---|---|---|
| 7,626,569 B2 | 12/2009 | Lanier | |
| 8,657,809 B2 * | 2/2014 | Schoepp | A61B 5/061 606/1 |
| 9,503,681 B1 | 11/2016 | Popescu et al. | |
| 2004/0263535 A1 | 12/2004 | Birkenbach et al. | |
| 2005/0020909 A1 | 1/2005 | Barrera et al. | |
| 2005/0288575 A1 * | 12/2005 | de la Barrera | A61B 34/20 600/423 |
| 2007/0238981 A1 * | 10/2007 | Zhu | A61B 90/36 600/424 |
| 2010/0137880 A1 * | 6/2010 | Nahum | A61B 34/30 606/130 |
| 2012/0078236 A1 * | 3/2012 | Schoepp | A61B 34/20 606/1 |
| 2012/0143049 A1 * | 6/2012 | Neubauer | A61B 90/98 600/424 |
| 2014/0022283 A1 | 1/2014 | Chan et al. | |
| 2014/0171959 A1 | 6/2014 | Yacono | |
| 2014/0236159 A1 * | 8/2014 | Haider | A61B 17/1626 606/88 |
| 2015/0077519 A1 | 3/2015 | Scott et al. | |
| 2015/0084990 A1 | 3/2015 | Laor | |
| 2015/0085095 A1 | 3/2015 | Tesar | |
| 2015/0305828 A1 | 10/2015 | Park et al. | |
| 2016/0127702 A1 | 5/2016 | Tsao et al. | |
| 2016/0191887 A1 * | 6/2016 | Casas | H04N 13/279 348/47 |
| 2016/0225192 A1 | 8/2016 | Jones et al. | |
| 2016/0246041 A1 | 8/2016 | Rappel | |
| 2016/0248994 A1 | 8/2016 | Liu | |
| 2016/0353055 A1 | 12/2016 | Popescu et al. | |
| 2017/0027651 A1 | 2/2017 | Esterberg | |
| 2017/0354342 A1 * | 12/2017 | Ben-Yishai | A61B 34/20 |

OTHER PUBLICATIONS

Andersen, D. et al., "Virtual annotations of the surgical field through an augmented reality transparent display", The Visual Computer, vol. 32, Issue 11, pp. 1481-1498, Published online May 27, 2015.

Birkfellner, W. et al., "The Varioscope AR—A Head-Mounted Operating Microscope for Augmented Reality", Medical Image Computing and Computer-Assisted Intervention—MICCAI 2000—Third International Conference, Pittsburgh, PA, USA, Oct. 11-14, 2000. Proceedings pp. 869-877.

D. Andersen, et al., Medical telementoring using an augmented reality transparent display. Surgery, 159(6), 1646-1653, doi: 10.1016/j.surg.2015.12.016—Jun. 1, 2016.

Gaskell, Adi, New System Brings Augmented Reality to the Operating Theatre, Sep. 23, 2015, http://adigaskell.org/2015/09/23/new-system-brings-augmented-reality-to-the-operating-theater/.

Modi, Yasha S. & Ehlers, Justis P., "Heads-up Vitreoretinal Surgery: Emerging Technology in Surgical Visualization—The future of retinal surgery", Retinal Physician, vol. 13, Issue: Jan. 1, 2016, pp. 26-29.

Odom, Jason "Two Doctors Simplify Spinal Surgery with the HoloLens", Feb. 14, 2017, pp. 1-5, https://hololens.reality.news/news/two-doctors-simplify-spinal-surgery-with-hololens-0175101/.

Venere, Emil, "Surgeons may get remote assistance with new 'tele mentoring' system", Aug. 25, 2015, pp. 1-4.

* cited by examiner

SURGICAL IMAGING SENSOR AND DISPLAY UNIT, AND SURGICAL NAVIGATION SYSTEM ASSOCIATED THEREWITH

CROSS REFERENCE TO RELATED APPLICATIONS

This application claims the benefit of, and priority to, Canadian Patent Application No. 2,983,780, filed Oct. 25, 2017, entitled "SURGICAL IMAGING SENSOR, DISPLAY UNIT, AND SURGICAL NAVIGATION SYSTEM ASSOCIATED THEREWITH," which is incorporated herein by reference in its entirety.

FIELD OF THE DISCLOSURE

The present disclosure relates to surgical instruments, tools and systems, and, in particular, to a surgical imaging sensor and display unit, and surgical navigation system associated therewith.

BACKGROUND

Visually open-access surgical sites, for example those employing a surgical access port or the like, generally rely on an overhead down-cavity surgical microscope or videoscope to display captured real-time images on a wall or stand-mounted display screen. Costly surgical microscopes or videoscopes used in these installations are generally mounted to a high end robotic arm in order to accurately pinpoint a location and orientation thereof, such that images captured thereby can be mapped in real-time to pre-operative imaging and surgical planning information and displayed accordingly. A surgical navigation system may also be used to monitor and track surgical site and surgical tool locations in real-time and provide augmented real-time intraoperative images based on these tracked locations, for example. These solutions served to provide an alternative to the traditional head-mounted microscopes and allow for the introduction of augmented surgical imaging.

Other surgical display tools have been proposed for the provision of visual aids. For example, U.S. Pat. No. 9,503,681 provides a method and system for remote collaboration and remote instruction utilizing computing devices at a trainee site and a mentor site, whereby annotations can be superimposed onto a trainee's view of a view field displayed using a simulated transparent display with augmented reality ("AR"). U.S. Patent Application Publication No. 2016/0246041 provides a surgical stereo vision system and method for microsurgery that enable hand-eye collocation, high resolution, and a large field of view, in that a display unit is located over an area of interest such that a human operator places hands, tools, or a combination thereof in the area of interest and views a magnified and augmented live stereo view of the area of interest with eyes of the human operator substantially collocated with the hands of the human operator.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a surgical display and imaging sensor unit, and surgical navigation system associated therewith, that overcome some of the drawbacks of known techniques, or at least, provides a useful alternative thereto. Some aspects of this disclosure provide examples of such systems and methods.

For instance, in accordance with some aspects of the present disclosure, a mobile surgical display and imaging sensor unit is described for use in a surgical environment to provide real-time visuals of a surgical site while also providing for an accurate tracking of the unit's position and orientation relative to the surgical site by leveraging tracking features of an associated intraoperative surgical navigation system. For instance, in some embodiments, accurate unit location tracking allows for the enhancement of unit-captured and displayed intraoperative images based on available preoperative and/or intraoperative imaging and/or tool location data, which can be effectively overlaid onto or otherwise combined with the captured images using global positioning information.

In some configurations, the display and imaging sensor unit can be interposed between the surgical site and the user's head and eyes to provide an enhanced line-of-sight display. In some such embodiments, reconfigurable imaging sensor optics can be reconfigured to adjust the display between a line-of-sight or near line-of-sight configuration, and an angled or redirected line-of-sight configuration (i.e. where the surgeon's line of sight can be angled relative to an imaging optical axis of the unit).

In yet other embodiments, the display and imaging sensor unit may be further or alternatively equipped with complementary imaging tools (broad and/or narrow spectrum light source(s) and/or sensor(s), filters, spectrometers, etc.), such as visible, infrared (IR), near IR, ultra violet (UV) and/or other spectrally selective imaging tools, thereby allowing for the complementary imaging of the surgical site using the unit, which complementary imaging may also benefit from the unit's positional tracking. For instance, the unit may provide not only for positionally tracked magnified visible imaging and display of the surgical site and/or portions thereof, but also, or alternatively, for positionally tracked spectral imaging and/or display of the surgical site and/or portions thereof. In doing so, all captured imaging data may be integrated with (e.g. embedded with or by, overlaid onto, nested with, annotated by or on, etc.) other preoperative and/or intraoperative data and/or images using the global positioning functions of the surgical navigation system.

In accordance with one broad aspect, there is provided a surgical system for conducting a surgical procedure on a surgical site, the system comprising: a mobile imaging sensor and display unit having a digital display screen and an image capture device structurally coupled thereto to be operatively aligned with the surgical site so to capture an image thereof to be rendered on the display screen; a tracking engine operable to automatically track a relative mobile unit location of the mobile imaging sensor and display unit relative to the surgical site; and a surgical image processing engine operable to associate an intraoperative surgical site location with the image based at least in part on the relative mobile unit location.

In one embodiment, the system further comprises a digital data storage medium having complementary location-specific surgical data stored therein, wherein the image processing unit is further operable to associate the complementary location-specific surgical data with the image based at least in part on the intraoperative surgical site location associated therewith.

In one embodiment, the complementary location-specific surgical data comprises location-specific pre-operative imaging data, and wherein the image processing unit is further operable to concurrently render the location-specific pre-operative imaging data with the image on the display screen.

In one embodiment, the tracking unit is further operable to track a surgical instrument location of a surgical instrument relative to the surgical site, and wherein the image processing unit is further operable to concurrently render complementary intraoperative data associated with the surgical instrument with the image on the display at least in part based on the surgical instrument location and the surgical site location.

In one embodiment, at least one of the surgical image processing unit or the tracking unit is at least partially implemented by a digital processor of the mobile unit.

In one embodiment, the mobile unit further comprises a mobile unit tracking marker fixedly disposed or disposable in relation thereto, and wherein the tracking unit comprises an external tracking sensor fixedly disposable at a distance from the mobile unit so to sense and thereby track a marker location of the mobile unit tracking marker relative thereto to derive the relative mobile unit location.

In one embodiment, the system further comprises a surgical site marker fixedly disposed or disposable in relation the surgical site, and wherein the tracking sensor concurrently senses and thereby tracks a location of the surgical site marker to derive the relative mobile unit location.

In one embodiment, the system further comprises a surgical site marker fixedly disposed or disposable in relation the surgical site, and wherein the tracking unit is at least partially implemented by a digital processor of the mobile unit so to sense and thereby track a relative location the surgical site tracking marker relative thereto to derive the relative mobile unit location.

In one embodiment, the image capture device comprises a digital camera.

In one embodiment, the image capture device comprises at least one of an infrared (IR), ultraviolet (UV), broad spectrum or narrow spectrum imaging device.

In one embodiment, the digital display screen is adjustably angled relative to the image capture device.

In one embodiment, the mobile imaging sensor and display unit is operatively disposable to provide a line-of-sight or near-line-of-sight display between the operator and the surgical site.

In one embodiment, the system further comprises an articulated arm operable to adjust a position of the imaging sensor and display unit relative to the surgical site.

In one embodiment, the articulated arm is selected from a manually or electrically actuated arm.

In one embodiment, the system further comprises a voice-recognition interface operable to receive voice-actuated commands for operating the imaging sensor and display unit.

In accordance with another broad aspect, there is provided a mobile image display device for use during a surgical procedure on a surgical site, the device comprising: a digital display screen; an image capture device structurally coupled thereto to be operatively aligned with the surgical site so to capture an image thereof to be rendered on the display screen; and a mobile unit tracking marker fixedly disposed or disposable in relation to the image capture device and externally trackable by a tracking sensor fixedly disposable at a distance therefrom so to sense and thereby track a relative location of the image capture device relative to the surgical site and associate an intraoperative surgical site location with the image based at least in part on the relative location.

In one embodiment, the display is further operable to concurrently render complementary location-specific surgical data with the image based at least in part on the intraoperative surgical site location associated with the image.

In one embodiment, the complementary location-specific surgical data comprises location-specific pre-operative imaging data.

In one embodiment, the display is further operable to concurrently render complementary intraoperative data associated with a surgical instrument with the image at least in part based on a concurrently tracked instrument location of the surgical instrument relative to the surgical site and the surgical site location.

In one embodiment, the device further comprises a surgical image processing engine operable to associate the intraoperative surgical site location with the image based at least in part on the relative location.

In one embodiment, the marker comprises a set of fiducial markers externally coupled in a fixed configuration to the device and thus trackable in tracking a 3D orientation of the device.

In one embodiment, the digital display screen is adjustably angled relative to the image capture device.

In one embodiment, the device further comprises a complementary imaging device distinct from the image capture device and structurally coupled to the display screen to be operatively aligned with the surgical site to capture complementary imaging data to be concurrently rendered on the display screen.

In one embodiment, the complementary imaging device comprises one or more illuminators or sensors to acquire the complementary imaging data.

In one embodiment, the complementary imaging device comprises at least one of an IR light source, a UV light source, a broad spectrum light source, a laser light source, an IR sensor, a UV sensor, or a narrow spectrum sensor.

In one embodiment, the display screen comprises a 3D display screen.

In one embodiment, the device further comprises a voice-recognition interface operable to receive voice-actuated commands for operating the device.

In accordance with another broad aspect, there is provided a mobile image display device for use during a surgical procedure on a surgical site, the device comprising: a digital display screen; an image capture device structurally coupled thereto to be operatively aligned with the surgical site so to capture an image thereof to be rendered on the display screen; and a resident location tracking engine operable to track a relative location of a location marker fixedly associated with the surgical site relative to the image capture device and associate an intraoperative surgical site location with the image based at least in part on the relative location.

In one embodiment, the display screen is further operable to concurrently render complementary location-specific surgical data with the image based at least in part on the intraoperative surgical site location associated with the image.

In one embodiment, the complementary location-specific surgical data comprises location-specific pre-operative imaging data.

In one embodiment, the display screen is further operable to concurrently render complementary intraoperative data associated with a surgical instrument with the image at least in part based on a concurrently tracked instrument location of the surgical instrument relative to the surgical site and the surgical site location.

In one embodiment, the digital display screen is adjustably angled relative to the image capture device.

In one embodiment, the device further comprises a complementary imaging device distinct from the image capture device and structurally coupled to the display screen to be operatively aligned with the surgical site to capture complementary imaging data to be concurrently rendered on the display screen, wherein the complementary imaging device comprises at least one of an IR light source, a UV light source, a broad spectrum light source, a laser light source, an IR sensor, a UV sensor, or a narrow spectrum sensor.

In one embodiment, the display screen comprises a 3D display screen.

These and other aspects, objects, advantages and features of the herein described embodiments will be described in greater detail below. For example, in accordance with one particular aspect, there is provided a Other aspects, features and/or advantages will become more apparent upon reading the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiment are often not depicted in order to facilitate a less obstructed view of these various embodiments of the present disclosure.

DETAILED DESCRIPTION

The embodiments described herein provide different examples of a surgical imaging sensor and display unit, and a surgical navigation system associated therewith. The tools, systems and methods described herein may be useful in the field neurosurgery, including oncological care, neurodegenerative disease, stroke, brain trauma, and orthopedic surgery. However, the subject matter of the present disclosure may extend or apply to other conditions or fields of medicine, and such extensions or applications are encompassed by the present disclosure. For example, the tools, systems and methods described herein encompass surgical processes that are applicable to surgical procedures for brain, spine, knee, and any other region of the body that will benefit from the use of a surgical navigation system, for example, within the context of access port or like surgical or medical procedures executed via a small open orifice to define and access a surgical cavity or site within the interior of an animal body, such as a human body.

Various tools, systems, apparatuses, devices, or processes are below-described and provide examples of trackable mobile imaging sensor and display units, and systems interfacing therewith and/or incorporating same, in accordance with embodiments of the present disclosure. None of the below-described embodiments limits any claimed embodiment; and any claimed embodiment may also encompass tools, systems, apparatuses, devices, or processes that may differ from the below-described examples. The claimed embodiments are not limited to tools, systems, apparatuses, devices, or processes having all of the features of any one of the below-described tools, systems, apparatuses, devices, or processes or to features common to some or all of the below-described tools, systems, apparatus, devices, or processes.

Furthermore, this Detailed Description sets forth numerous specific details in order to provide a thorough understanding of the various embodiments described throughout the present disclosure. However, it will be understood by those of ordinary skill in the art that the embodiments described herein may be practiced without these specific details. In other instances, well-known methods, procedures and components have not been described in detail so as not to obscure the embodiments described herein.

Figure 1:
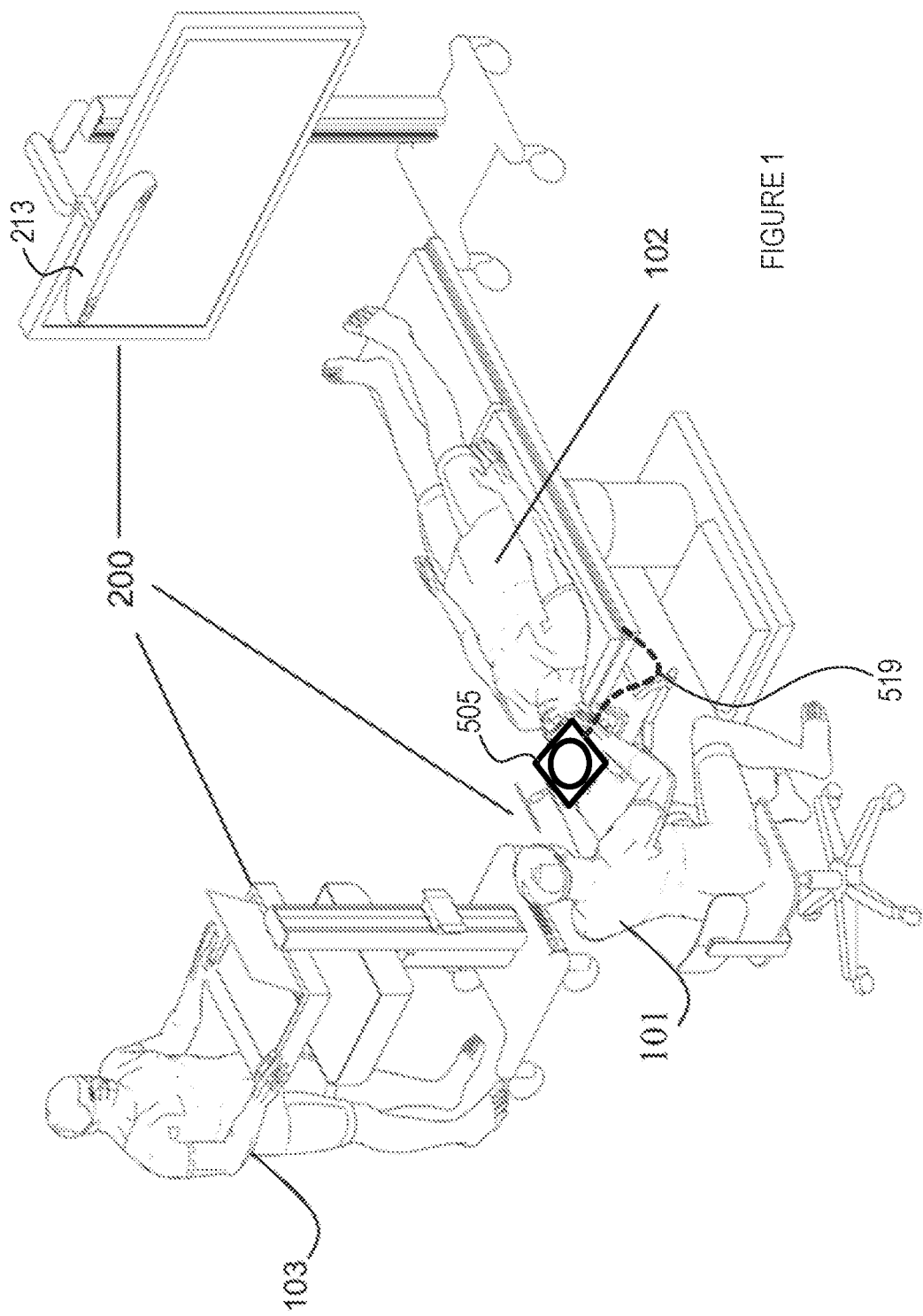
FIG. 1 is a diagram of a medical navigation system comprising a trackable mobile imaging sensor and display unit, when used in an exemplary surgical environment, in accordance with some embodiments of the present disclosure.
Figure 2:
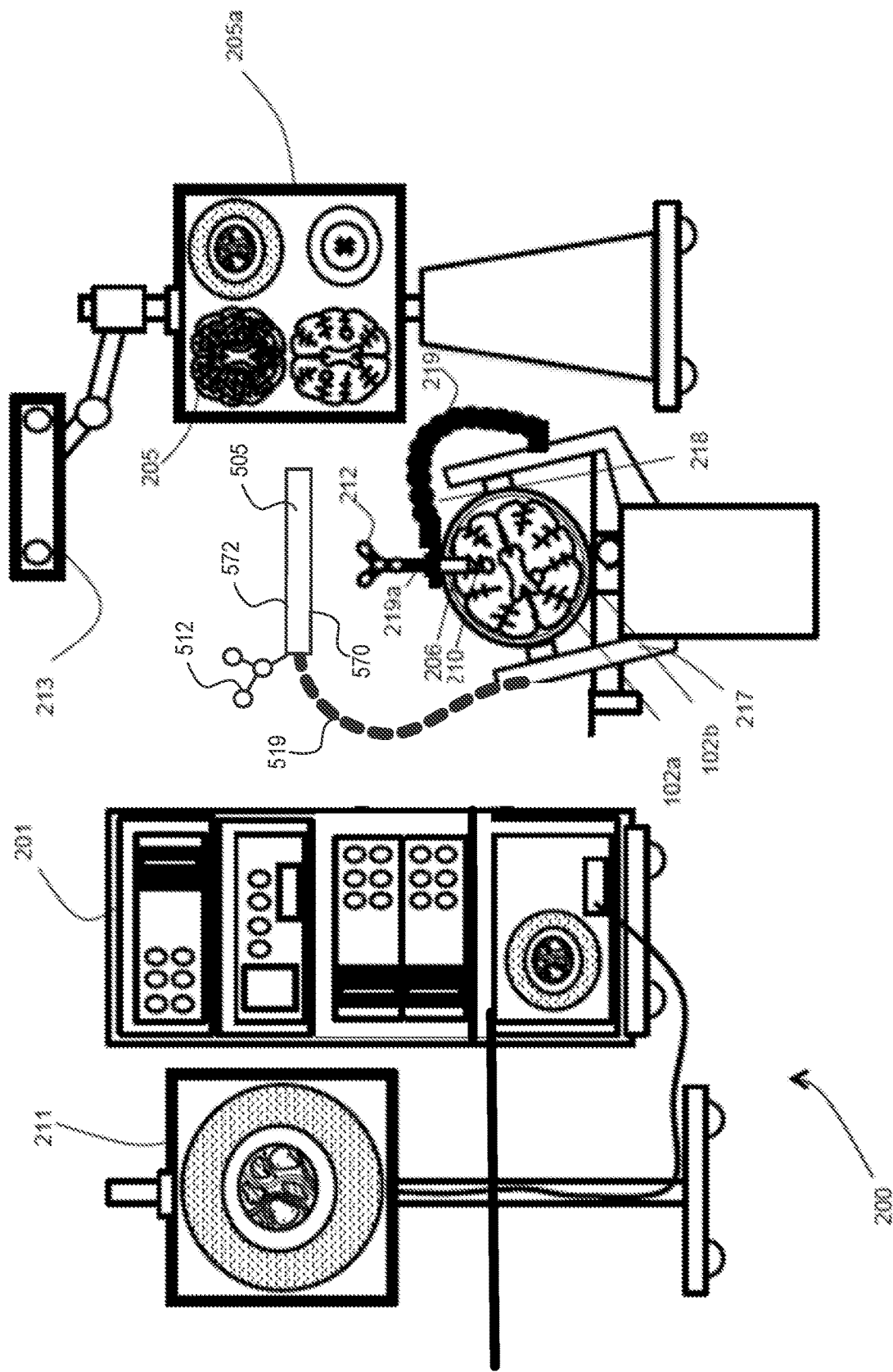
FIG. 2 is a diagram illustrating an access port-based surgical procedure being conducted by way of a navigation system, comprising a trackable mobile imaging sensor and display unit and a patient reference device, in accordance with some embodiments of the present disclosure.

With reference to FIGS. 1 and 2, and in accordance with one embodiment, a trackable mobile imaging sensor and display unit, generally referred to using the numeral 505, will now be described within the context of an exemplary port-based surgical system. As noted above, the trackable mobile imaging sensor and display unit, described herein within the context of a port-based surgical system and associated tracking/navigation system, are also be amenable to other similar or alternate surgical systems and procedures, without departing from the general scope and nature of the present disclosure. Namely, the utility and applicability of the herein-described embodiments are not limited to port-based and/or neurological procedures, but rather, may prove particularly useful and desirable in a number of surgical environments in which a tracked mobile imaging unit is operable to capture and render real-time images of a surgical site, e.g., down-port surgical images, and mapped onto, or otherwise locationally correlated with, other procedure-specific, e.g., pre-operative and/or intraoperative, images and/or locations.

In the illustrated examples, the surgical system encompasses an exemplary surgical navigation system 200 operable to track various patient reference devices, in an environmental context, such as an operation room (OR). The system 200 supports, facilitates, and enhances minimally invasive access port-based surgery using a minimally invasive access port-based surgical procedure, though non port-based procedures may equally be considered herein as above noted.

By example only, a surgeon 101 conducts a minimally invasive access port based surgery on a subject, such as a patient 102, in an OR environment. The navigation system 200 generally includes an equipment tower 201 (which may be reduced, in some embodiments, to one or more computerized devices and/or appliances having sufficient computational processing and/or data storage resources to support the surgical procedure and equipment at hand), a tracking system or unit 213 to define and/or track a location of the surgical site (e.g. via access port or other surgical tool or equipment tracking) and/or various procedural tools or equipment associated therewith, and a trackable mobile imaging sensor and display unit 505, tracked by the tracking system 213 and operable, as noted above, to capture images of the surgical site and render images thereof back to the surgeon 101, for example. For example, the mobile unit 505 may generally comprise one or more imaging sensors (e.g. see image capture sensor or camera 560 and optional complementary imaging sensors 562 shown in FIG. 3) disposed on a patient-facing side 570 of the unit 505, and one or more image displays (e.g. see image display screen 564 of FIG. 3) on a surgeon or operator-facing side 572 of the unit 505, thereby allowing, in some configurations, for line-of-sight or near line-of-sight imaging of the surgical site (i.e. where the mobile unit 505 is interposed between the surgeon and the surgical site for direct or near direct line-of-sight visibility).

The system may further include a wall or stand-mounted display or monitor 205, 211 for displaying a video image of the captured surgical site or related information. By example only, an operator 103 is also present to operate, control, and provide assistance for the system 200. The system may further include a robotic arm (not shown) to support and control one or more precision surgical tools, imaging devices or the like.

With particular reference to FIG. 2, the equipment tower 201 is generally mountable on a frame, e.g., a rack or a cart, and is configured to accommodate a power supply, e.g., an AC adapter power supply, and at least one computer or controller operable by at least one a set of instructions, storable in relation to at least one non-transitory memory device, corresponding to at least one of surgical planning software, navigation/tracking software, or optional robotic software for managing an optional robotic arm and at least one instrument used during the procedure. For example, the computer comprises at least one of a control unit and a processing unit, such as control and processing unit 300 or 430 schematically shown in FIGS. 8 and 4, respectively. In the illustrated embodiment, the equipment tower 201 comprises a single tower configured to facilitate coupling of the mobile unit 505 with optional displays 211 and 205 and/or at least one piece of equipment. However, other configurations are also encompassed by the present disclosure, such as the equipment tower 201 comprising dual towers configured to facilitate coupling of the mobile unit 505, etc. The equipment tower 201 is also configurable to accommodate an uninterruptible power supply (UPS) for providing emergency power. Furthermore, different embodiments may accommodate either or both wired and wireless connections between various system components, for example, to relay image capture and/or processing data to and from the mobile unit 505 and optional surgical tools and/or probes, tracking data from the tracking system 213, and image/data rendering data to and from the mobile and other optional displays, for example.

To maintain constant positioning of the patient's anatomy of interest during a given procedure, the patient's anatomy may be held in place by a holder appropriate for the procedure in question. For example, in a port-based neurosurgical procedure, such as that illustrated in FIG. 2, a patient's head can be retained by a head holder 217. A craniotomy is performed, a dura flap is formed and retracted, and the access port 206 and introducer 210 can then be inserted into the patient's brain 102b, and the planned procedure is executed while the patient's head remains effectively immobile.

As noted above, the system also includes a tracking system 213 that is generally configured to track the mobile unit 505 and generally, at least one instrument, such as a surgical instrument or tool, or patient reference device such as the access port itself or introducer (e.g. to define a surgical site location and/or monitor any displacement thereof during the procedure, as appropriate). In FIGS. 1 and 2, the tracking system is initially utilized to track the access port 206 and introducer 210 while the access port is being introduced within the patient's brain so to ultimately locate and define the surgical site and surrounding surgical cavity. However, other sensored or non-sensored intra-operative surgical tools, such as, but not limited to, inner-cavity pointing tools, suction tools, tissue probes (e.g. Raman, OCT probes, etc.), resection tools and the like, are also advantageously tracked by the tracking system to enhance accuracy and precision of executed operative procedures. Instrument tracking can thus significantly assist the surgeon 101 during the minimally invasive access port-based surgical procedure (or like procedures) both in guiding and confirming procedural actions, but also in aligning real-time surgical site imaging and characterization, as detailed below with reference to the trackable mobile imaging sensor and display unit 505, with pre-operative imaging data. Accordingly, tracking sensored tools along with the mobile imaging unit 505 can significantly benefit enhanced or complementary inner-cavity imaging, localization, characterization and/or mapping.

Accordingly, the tracking system 213 is configured to track and determine, e.g., in real-time by way of a set of instructions corresponding to tracking software and storable in relation to at least one non-transitory memory device, the location of the one or more tracked instruments during the surgical procedure.

In the illustrated embodiment, the tracking system 213 generally comprises at least one sensor (not shown) for detecting at least one fiducial marker 512, 212, disposable in relation the one or more OR items (e.g. mobile imaging unit 505) and/or surgical instruments (introducer 210), respectively, to be tracked. In one example, the tracking system 213 comprises a three-dimensional (3D) optical tracking stereo camera, such as a Northern Digital Imaging® (NDI) optical tracking stereo camera, which can be configured to locate reflective sphere tracking markers 512, 212 in 3D space. In another example, the tracking camera 213 may be a magnetic camera, such as a field transmitter, where receiver coils are used to locate objects in 3D space, as is also known in the art. Accordingly, location data of the mobile imaging unit 505, access port 206, introducer 210 and its associated pointing tool, and/or other tracked instruments/tools, may be determined by the tracking camera 213 by automated detection of tracking markers 512, 212 placed on these tools, wherein the 3D position and orientation of these tools can be effectively inferred and tracked by tracking software from the respective position of the tracked markers 512, 212.

In the illustrated embodiment of FIG. 2, the secondary displays 205, 211 can provide an output of the tracking camera 213, which may include, but is not limited to, axial, sagittal and/or coronal views as part of a multi-view display, for example, and/or other views as may be appropriate, such as views oriented relative to the at least one tracked instrument (e.g. perpendicular to a tool tip, in-plane of a tool shaft, etc.). These and other views may be considered in various single or multi-view combinations, without departing from the general scope and nature of the present disclosure. In some embodiments, such views may be further or alternatively rendered on the mobile imaging sensor and display unit 505 as main or selectable views, or again as visible enhancements (e.g. overlays, annotations, etc.) to line-of-sight images captured by the unit 505, e.g. mapped thereto based on concurrently tracked relative positions thereof to provide an augmented reality (A/R) experience. Likewise, the image rendered on the mobile unit 505 may be replicated on displays 205, 211 to provide a live "line-of-sight" view of the surgical site for different individuals present in the OR.

Still referring to FIG. 2, minimally invasive brain surgery using access ports is a recent method of performing surgery on brain tumors. In order to introduce an access port 206 into a brain, such as the patient's brain 102b, of a patient head's 102a, an introducer, e.g., the introducer 210, comprises an atraumatic tip disposable within the access port 206 to facilitate positioning the access port 206 within the patient brain 102b. As noted above, the introducer 210 further comprises at least one fiducial marker 212 for facilitating tracking by the tracking system 213. Generally, tracked tools such as introducer 210 will include a plurality of fiducial markers to enhance trackability in 3D space.

After the introducer 210 and the access port 206 are inserted into the brain 102b, the introducer 210 is removed to facilitate access to the tissue of the brain 102b through the central opening of the access port 206. However, after the introducer 210 is removed, the access port 206 is no longer being tracked by the tracking system 213. However, the access port 206 is indirectly trackable by way of additional pointing tools (not shown) configured for identification by the navigation system 200.

In the illustrated embodiment of FIG. 2, the navigation system 200 further comprises a guide clamp 218 for retaining the access port 206. The guide clamp 218 is configured to optionally engage and disengage the access port 206, eliminating the need to remove the access port 206 from the patient 102. In some embodiments, the access port 206 is configured to slide up and down within the guide clamp 218 in a closed position. The guide clamp 218 further comprises a locking mechanism (not shown), the locking mechanism being attachable or integrable in relation to the guide clamp 218, and the locking mechanism being optionally manually actuable, e.g., using one hand as further below described.

The navigation system 200 further comprises an articulating arm 219, such as a small articulating arm, configured to couple with the guide clamp 218. The articulating arm 219 comprises up to six (6) degrees of freedom for facilitating positioning of the guide clamp 218. The articulating arm 219 is attachable at a location in relation to the head holder 217, or in relation to any other suitable patient support structure, to ensure, when locked in place, that the guide clamp 218 is fixed in relation to the patient's head 102a. The articulating arm 219 comprises an interface 219a disposable in relation to the guide clamp 218, wherein the interface 219a is at least one of flexible or lockable into place. Flexibility of the interface 219a facilitates movability of the access port 206 into various positions within the brain 102b, yet still maintains rotatability about a fixed point.

As will be further detailed below, the navigation system 200 further comprises an articulating arm 519, such as a small articulating arm, configured to couple with the mobile imaging unit 505. The articulating arm 519 may again comprise up to six (6) degrees of freedom for facilitating positioning of the mobile unit 505. The articulating arm 519 is also attachable at a location in relation to the head holder 217, or in relation to any other suitable support structure. The articulating arm 519 allows for controlled mobility of the mobile unit 505 while also optionally allowing to lock it in place once an optional position has been set. Regardless, the surgeon may occasionally move the mobile unit 505 to improve image capture and surgical site visibility, alignment, ergonomics, line-of-sight imaging and the like, all while being tracked by the tracking system 213 so to compute and adjust a relative position/orientation of the images captured and rendered thereby, and adjust alignment of complementary imaging and/or augmented reality data/images/overlays accordingly. In some embodiments, the articulating arm 519 consists of a manually articulated arm in a relative mobile unit position and/or orientation can be manually adjusted by the surgeon and/or OR staff to provide improved line-of-sight, user ergonomics and/or comfort, and like considerations. In other embodiments, the articulating arm 519 may rather consist of an electronic (robotic) arm that can be remotely actuated via an electrical or wireless interface. For instance, providing remote actuation of the articulating arm 519 may reduce direct user interaction with the mobile unit 505 thereby reducing the likelihood of damage, contamination, soiling and the like. Accordingly, the surgeon and/or other OR staff may effectively reposition and/or reorient the mobile unit 505 without directly manually interfacing with the mobile unit 505 or articulating arm 519. Such robotic controls and/or interfaces may include, but are not limited to, distinct remote control interfaces, computerized graphical user interfaces, voice-recognition and actuation interfaces and/or controls, and the like, to name a few. A robotic arm configuration may also allow for direct tracking of the arm's movement, position and orientation, thereby replacing or contributing to a tracking of the mobile unit's position/orientation. In configurations invoking active voice controls, voice recognition may also be invoked to control operation of the mobile unit 505 itself, as further discussed below, not only to adjust a position and/or orientation of the mobile unit 505, but also, or alternatively, control or adjust imaging, image rendering, A/R, visual analytics, data displays or like functions or features of the mobile unit 505. Such voice control features may replace or otherwise complement touchscreen commands and/or tethered/wireless physical control interfaces (e.g. buttons, mouse, keypad, toggles, trackballs, etc.).

In yet other embodiments, the mobile unit 505 may be configured to track a relative position of the surgeon's head, for example, and automatically adjust a position/orientation of the mobile unit accordingly. For example, a surgeon-facing camera of the mobile unit 505 could be leveraged, in combination with machine vision or other resident tracking mechanisms, to track a relative motion of the surgeon's head, eyes or other relevant body parts, and respond by reconfiguring the mobile unit 505 accordingly. Such automated tracking and adjustment processes may ultimately allow the surgeon to avoid or reduce manual unit interventions while maintaining improved or optimized alignment/ergonomics.

With continued reference to FIG. 2, the navigation system 200 may further or alternatively comprise a plurality of wide-field cameras, e.g., two additional wide-field cameras (not shown) being implemented with video overlay information, wherein one camera is mountable in relation to the mobile unit 505 (e.g. overhead camera) and the other camera is mountable in relation to the navigation system 213 (i.e. within the context of an electromagnetic tracking system). In the case of the navigation system 213 comprising an optical tracking device, a video image can be directly extracted therefrom. Video overlay information can then be used to enhance available intraoperative information, for example, by providing an image displaying a physical space and confirming tracking system registration alignment and optional corresponding text and/or indicia, an image displaying a motion range of the mobile unit 505 and optional corresponding text and/or indicia, and/or an image displaying a guide head positioning and a patient positioning and optional corresponding text and/or indicia.

Other image overlays, as will be described in greater detail below, may further include intraoperative cavity imaging and/or characterization data (e.g. colour mapping, partial image transparency overlay, text and/or indicia), such as provided by a sensored tool as described in Canadian Patent Application No. 2,957,977 (the entire contents of which are hereby incorporated herein by reference), for example including, but not limited to, real-time inner cavity images (e.g. visible, near infrared (IR), etc.) provided by tool tip mounted camera(s), real-time inner cavity pressure readings (e.g. localized fluid pressure readings, pressure gradients, pressure mappings, etc.) provided by tool tip mounted pressure sensor(s) and/or sensor arrays, and other such readings of interest given the application at hand. Using such real-time intraoperative inner cavity imaging and characterization data may not only enhance other intraoperative images, such as those rendered by overhead and/or mobile unit 505 cameras, but also seamlessly integrate with pre-operative images and/or data, for instance, acquired pre-operatively using one more imaging techniques. Accordingly, the surgeon and/or other surgical equipment operator can execute procedures and/or actions with greater clarity, certainty and visibility, thus leading to improved outcomes and risk reduction.

Figure 3:
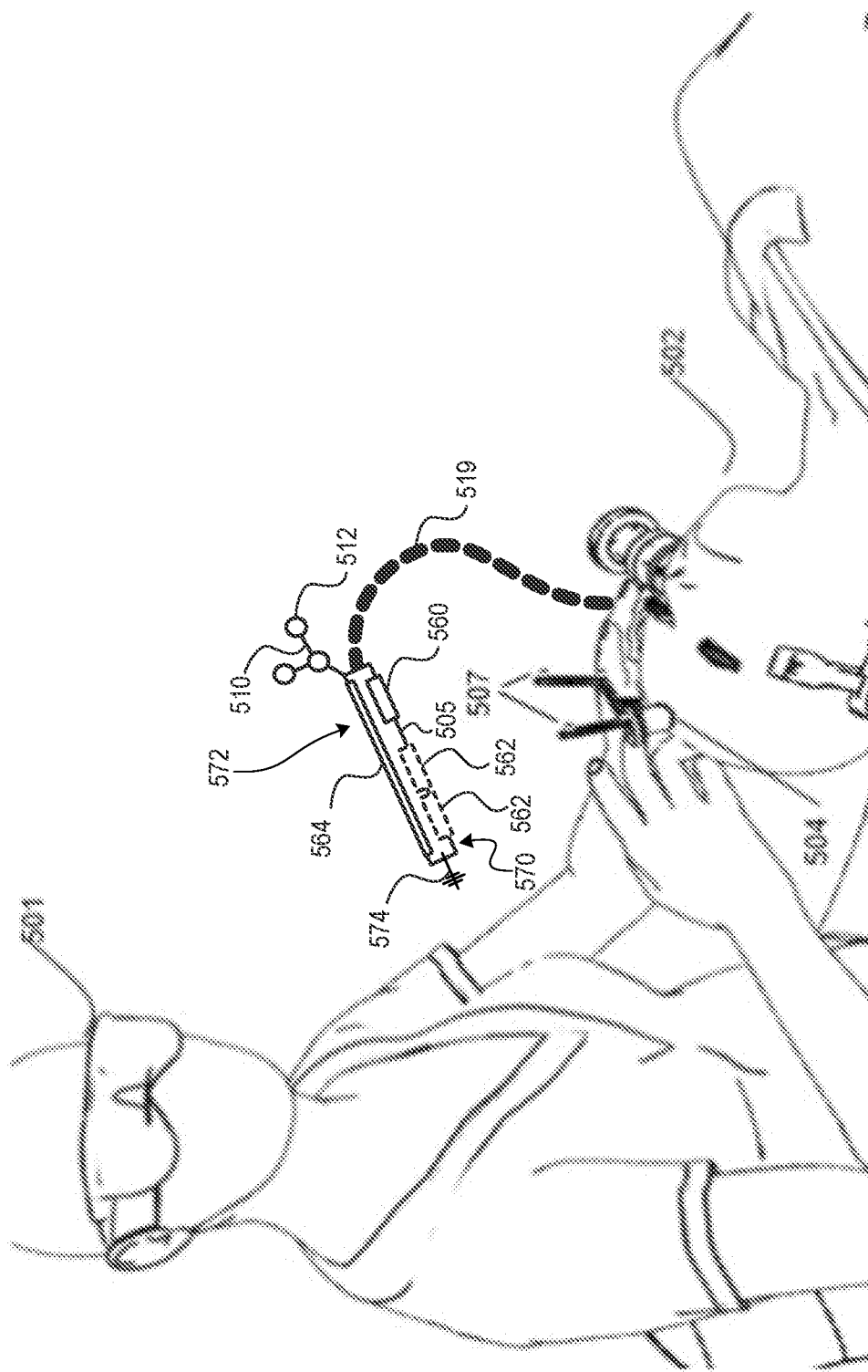
FIG. 3 is a diagram of a mobile imaging sensor and display unit, in accordance with one embodiment, used within the context of an access port-based surgical procedure being conducted by way of a navigation system as shown, for example, in FIG. 2.
Figure 4:
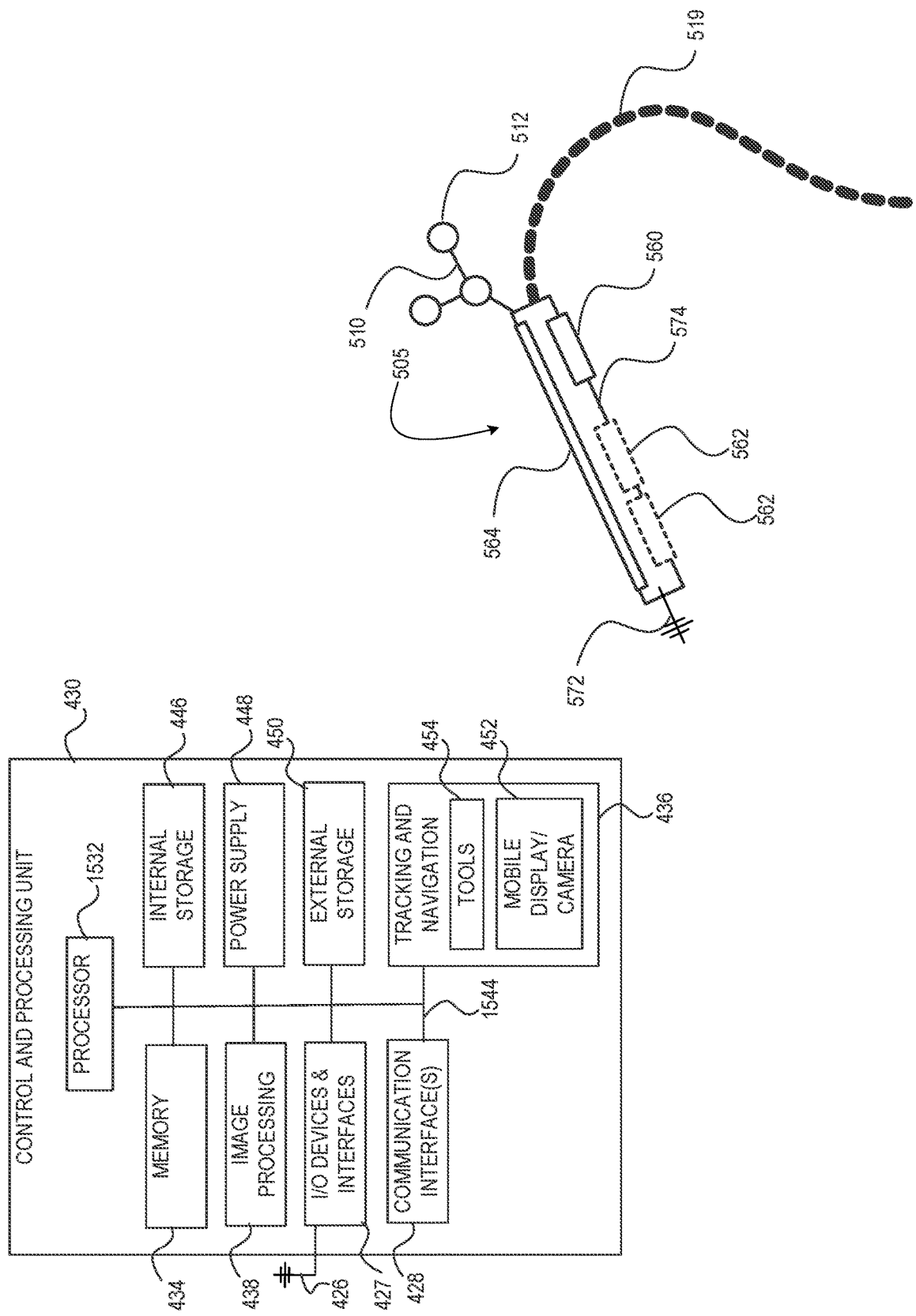
FIG. 4 is a schematic diagram of the trackable mobile imaging sensor and display unit of FIG. 3, and an associated control and processing unit, in accordance with an embodiment of the present disclosure.

FIG. 3 provides another diagram of an access port-based surgical procedure conducted by way of the navigation system 200, in accordance with some embodiments of the present disclosure, in which a mobile imaging sensor and display unit 505, as also shown in FIG. 4, is used to provide line-of-sight or near line-of-sight imaging of the surgical site. In this example, a surgeon 501 is resecting a tumor from the brain of a patient 502 through an access port 504. The mobile image capture and display unit 505 is coupled with a manually or mechanically driven articulated arm 519 to a patient support or other generally fixed structure and articulated to position/orient the mobile unit 505, in this example, in a direct or near direct line-of-sight configuration. Positioned as such, a primary image sensor 560 (e.g. camera and related magnification optics with sufficient magnification to allow for enhanced visibility down port 504) can be used to capture down-port images/video of the surgical site, and render these images in real-time on a display screen 564 of the unit 505. Accordingly, the surgeon can maintain the direct line-of-sight benefit of otherwise cumbersome head-mounted microscopes, while also optionally adjusting the position and orientation of the mobile unit 505 to suit viewing and/or ergonomic preferences, for example, via manual, robotized and/or voice control. Complementary imaging sensors and/or imaging emitters 562 (interchangeably referred to herein as image or imaging sensors, emitters or illuminators, probes, devices, etc.) may also be included, for example, to provide complementary or alternative imaging capabilities to the mobile unit 505, such as infrared, near infrared, UV or other broad spectrum imaging capabilities, or again laser or other narrow spectrum imaging capabilities that may further include optical output devices (e.g. lasers, spectrally-selective illuminators and/or sensors, or the like) to accommodate such complementary imaging capabilities. Other imaging tools combining specific illumination/probing optics or other probing waveforms (e.g. ultrasound) and associated image sensing capabilities may also be considered, for example, to be jointly or interchangeably disposed and operated from a patient-facing side 570 of the unit 505. Accordingly, the mobile unit 505 may be used not only for singular imaging capabilities (e.g. magnified or enhanced visible, IR or UV image capture), but also to acquire (and display) complementary imaging data such as may be usable within the context of medical fluorescence, blood profusion imaging, Raman spectroscopy, optical coherence tomography (OCT), etc. These and/or other complementary camera/illumination payloads (i.e. illuminators and/or imaging sensors) can be considered to benefit imaging capabilities provided to the unit (and other surgical displays) while minimizing obstructiveness thereof by being collocated on the patient-facing side of the unit 505. The unit 505 may further allow an operator to switch or toggle between different imaging views not only based on different magnifications (e.g. micro, macro, zoom), but also different imaging modalities as provided by the unit's different complementary imaging illumination and/or sensing capabilities.

In yet other embodiments, the unit 505 may further or alternatively include one or more imaging cameras (e.g. stereoscopic camera(s)) to capture 3D or like (i.e. depth descriptive) images, and may likewise include a 3D display so to display 3D or like images. For example, while a traditional image displays may be considered in which the operator also wears 3D glasses, lenticular or like glasses-free 3D displays may also be considered to provide for a more convenient operation.

The mobile unit 505 further comprises a wired and/or wireless transducer 510, externally illustrated herein as antenna 574 for ease of description, but clearly generally configured for internal integration, to relay capture image data to and from the navigation system 200, related control unit(s), and the like, in order to not only display captured images directly on the display 564, but also allow for dynamic tracking of the mobile unit 505 and positional alignment of direct and/or external pre- and intra-operative imaging and like data, for example. Likewise, images captured by the mobile unit 505 may be rendered on an external visual display, such as displays 205, 211 shown in FIG. 2.

As introduced above, the procedure illustrated in FIG. 3 may involve disposing passive (or active) fiduciary or like markers, 507, 512, e.g., spherical markers fixedly mounted to a marker tree 510 or like structure, in relation the access port 504 and the mobile unit 505 for facilitating their tracking (location of these tools) by the tracking system (e.g. tracking system 213 of FIG. 2). The active or passive fiduciary markers, 507, 512, are sensed by sensors of the tracking system 213, whereby identifiable points are provided. A tracked instrument is typically indicated by sensing a grouping of active or passive fiduciary markers, 507, 512, whereby a rigid body, such as a tool, is identified by the tracking system 213, and whereby the position and orientation in 3D of a tracked instrument, such as a tool, is determinable. Namely, a substantially rigid tool can be tracked in 3D space to effectively locate and orient the tool and its various segments and constituent components, provided such segments/components are previously defined and stored against the tracked tool type. Accordingly, a tracked tool may invoke not only general tracking, but also tracking, for example, of the tool's tip or body, and any sensors, as will be detailed below, that may be operatively coupled thereto in a designated configuration (e.g. at or near a tool tip, angled relative to a tool tip or shaft, displaced and/or angled relative to other tool-mounted sensors, etc., within the context of tool, or again on one or another of the mobile unit's surfaces, a fixed or adjustable and thereby trackable orientation or alignment of a given sensor mounted thereon, etc.). Typically, a minimum of three active or passive fiduciary markers, 507, 512, are placed on a tracked tool or instrument to define the instrument. In the several figures included herewith, four active or passive fiduciary markers, 507, 512, are used to track each tool, by example only.

In one particular example, the fiduciary markers comprise reflectosphere markers in combination with an optical tracking system to determine spatial positioning of the surgical instruments within the operating field. Differentiation of the types of tools and targets and their corresponding virtual geometrically accurate volumes can be determined by the specific orientation of the reflectospheres relative to one another giving each virtual object an individual identity within the navigation system. The individual identifiers can relay information to the system as to the size and virtual shape of the tool within the system. The identifier can also provide information such as the tool's central point, the tools' central axis, the tool's tip, etc, or in the case of the mobile unit 505, the unit's 3D position and angular orientation relative to the surgical site (e.g. the unit's distance and line-of-sight thereto). Other imaging characteristics may be used in conjunction with the tracking data to identify a particular image target and representation. For example, static and or adjustable optical properties of the unit's primary imaging sensor 560 (e.g. camera) and/or complementary sensors 562 may include relative imaging view angle (e.g. directly extrapolated from an orientation of the unit 505 as a whole or alternatively accessed from an angular disposition of an adjustable camera, see unit 505B of FIG. 5B), focus length, depth of field, view angle, resolution, or the like. Other imaging parameters may include, but are not limited to, various optical and/or spectral imaging parameters such imaging filters (e.g. for spectral imaging, fluorescence, spectroscopy, IR, UV, Raman, etc.), optical probe wavelength or spectrum (e.g. for spectrally selective imaging via laser probe, UV light probe, IR probe, etc.), or again alternative imaging capabilities as will be readily appreciated by the skilled artisan.

The virtual tool and unit may also be determinable from a database of tools provided to the navigation system 200. The marker positions can be tracked relative to an object in the operating room such as the patient. Other types of markers that can be used may include, but are not limited to, radio frequency (RF), electromagnetic (EM), pulsed and un-pulsed light-emitting diodes (LED), glass spheres, reflective stickers, unique structures and patterns, wherein the RF and EM would have specific signatures for the specific tools or mobile unit to which they would be attached. The reflective stickers, structures, and patterns, glass spheres, LEDs could all be detected using optical detectors, while RF and EM could be detected using antennas. Advantages to using EM and RF tags may include removal of the line of sight condition during the operation, where using the optical system removes the additional noise from electrical emission and detection systems.

In a further embodiment, printed or 3D design markers can be used for detection by an auxiliary camera and/or external scope. The printed markers can also be used as a calibration pattern to provide distance information (3D) to the optical detector. These identification markers may include designs such as concentric circles with different ring spacing, and/or different types of bar codes. Furthermore, in addition to using markers, the contours of known objects (e.g., side of the port, top ring of the port, shaft of pointer tool, etc.) can be made recognizable by the optical imaging devices through the tracking system 213. Similarly, or in addition thereto, structural information relating to each tool (size, dimensions, distance and geometric orientation relative to markers) may be used to extrapolate the position and orientation various tool segments, such as the tool tip, and various sensors that may be operatively mounted thereon or associated therewith, as noted above. In that respect, the designated shape and mechanical volume of the mobile unit 505 can be used to recognize an orientation and/or distance of the unit 505 relative to the tracking system 213, for instance, given the relative image size and silhouette of the tracked unit which can be used to provide some indication of distance and orientation.

In yet further embodiments, positional data calculated directly by the mobile unit 505, such as resident inertial or gyroscopic sensors, inclinometers, accelerometers or the like, may be used to locally track a relative position and/or orientation of the unit 505, either alone or in combination with other tracking resources noted above. For example, an initial position/orientation (i.e. origin) of the unit 505 may be precisely defined in an initialization/calibration phase, for instance along with input and output optic calibrations and optimizations to promote accurate correlation of captured images within the actual physical space of the surgical environment/site. The mobile unit's onboard self-locating resources, as noted above, could then be leveraged to compute and/or support computation of the unit's displacement and reorientation over time. For example, in one implementation, the onboard positional sensors may be used to track, monitor, flag and/or record a relative displacement and/or reorientation of the unit 505 during use, which may complement tracking system data and/or alert system users of any discrepancies, the potential need for system recalibration, or like concerns.

In yet other embodiments, the unit's onboard camera and/or optical sensors can be used, alone or in combination, to track its own position/orientation relative to other OR tools and/or equipment. For example, where the position and orientation of an access port has been accurately determined, as described above, within the context of a given surgical plan or procedure, and where the surgical port caries a number of tracking markers, such as markers 507, the unit's onboard optical sensors may be used, in combination with an onboard or remotely associated tracking software, to track a relative distance and orientation of the unit 505 relative to the access port, particularly as the access port and surgical site in general will maintain a fixed position and orientation throughout the procedure. This may be particularly useful where a line-of-sight between the mobile unit 505 and external tracking system 213 can be obscured or otherwise inconveniently maintained during a procedure. Likewise, a mobile unit-based tracking system may be used to locate and monitor other intraoperative tools during the procedure, particularly given the general alignment and common line-of-sight disposition of the mobile unit 505 relative to the surgical site.

As will be appreciated by the skilled artisan, while the above lists a number of tracking techniques and related marker types, other known and future techniques may also be considered within the present context to support and enhance operation of the mobile unit 505 and optionally tracked surgical tools, i.e. sensored tools, described herein. Namely, the tracking technique for each instrument will generally allow for the tracking of the instrument's position and orientation within a given frame of reference, in which the position and orientation can be tracked, relayed and/or rendered on the surgical system's one or more displays to visually locate the tool, or data/images acquired thereby, within the context of the procedure taking place and/or any otherwise available pre-operative and/or intraoperative images/details.

Figure 6A:
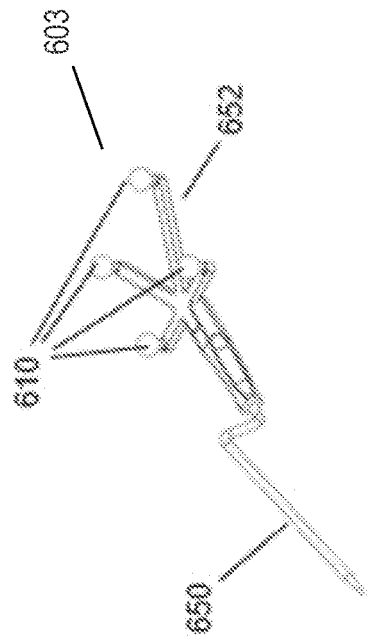
FIGS. 6A to 6D are perspective views of respective trackable pointing tools having distinctly configured tracking markers equally amenable for tracking a mobile imaging sensor and display unit as shown in FIGS. 3 and 4, in accordance with different embodiments of the present disclosure.

With reference to FIG. 6A, and in accordance with one illustrative embodiment, a perspective view of an exemplary surgical tool 601 is provided, wherein the tool 601 comprises a rigid pointer or pointing tool 600 rigidly coupled to a set of tracking markers 610 fixedly disposed relative thereto in a designated configuration geometry that is recognizable by the tracking system (e.g. tracking system 213 of FIG. 2, or again an onboard or distributed tracking system associated with a mobile imaging sensor and display unit as described herein). In this example, the markers 610 are fixedly coupled to the pointing tool 600 via respective connector beams 615 attached to respective laterally extending arms 620 forming a box-like configuration in a plane of the tool's handle 625.

Figure 6C:
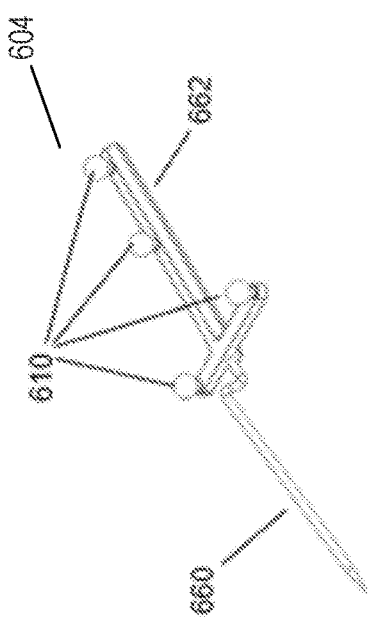
Figure 6B:
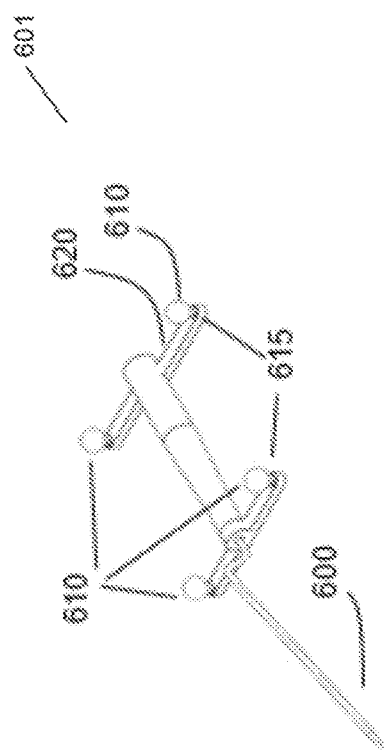

FIG. 6B, provides another example of a tracked surgical tool 602, again defined by a pointer or pointing tool 640 and related tracking markers 610, this time rigidly coupled to the pointing tool 640 via a laterally splayed support arm structure 642.

Likewise, FIG. 6C provides another example of a tracked surgical tool 603, again defined by a pointer or pointing tool 650 and related tracking markers 610, this time rigidly coupled to the pointing tool 650 via an intersecting support arm structure 652.

Figure 6D:
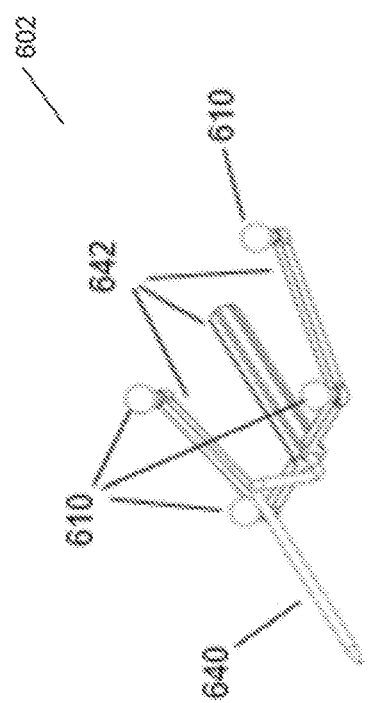
Figure 6E:
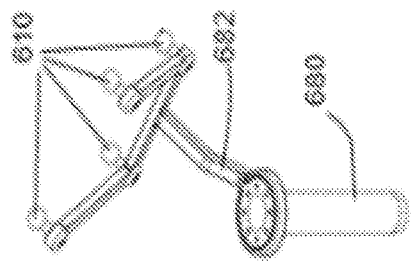
FIGS. 6E to 6H are perspective, front elevation, side and top plan views, respectively, of a trackable surgical access port having a set of tracking markers, in accordance with an embodiment of the present disclosure.
Figure 6G:
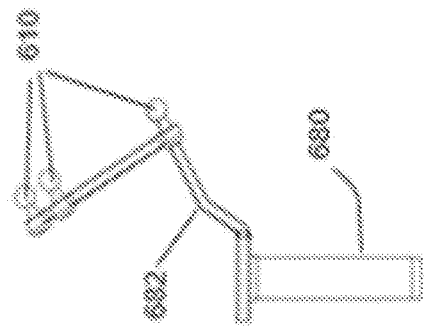
Figure 6F:
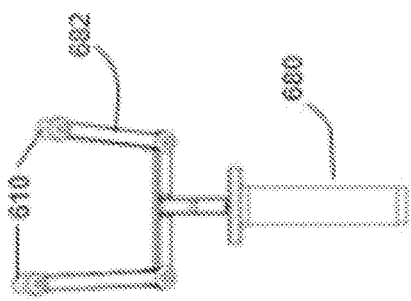
Figure 6H:
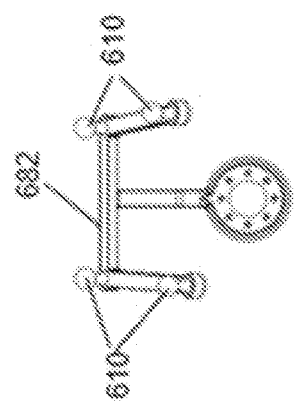

FIG. 6D provides yet another example of a tracked surgical tool 604, again defined by a pointer or pointing tool 660 and related tracking markers 610, this time rigidly coupled to the pointing tool 660 via a T-shaped support arm structure 662.

In each of the examples shown by FIGS. 6A to 6D, the tracked tool includes a pointing tool, though other surgical instruments may also be considered within the present context to provide a like effect. For instance, a suction or resection tool, or other surgical probe, may also be considered in which tracking is effectively provided by appropriate markers and a tracking system, and whereby a position and orientation of the tracked tool may be adequately tracked, relayed and rendered during the procedure. Accordingly, while these marker configurations are shown within the context of a pointing or like tool, similar marker configurations may be used to effectively track and monitor a location and orientation of a mobile imaging sensor and display unit, as described herein.

For completeness, and with reference to FIGS. 6E to 6H, other surgical devices may also be intraoperatively tracked, as noted above. For example, these figures respectively provide perspective, front elevation, side and top plan views of a surgical port 680 rigidly associated with a corresponding set of markers 610 coupled thereto via a support structure 682. The illustrated arrangement enables clear visibility of the fiducial or tracking markers 610 to the tracking system 213, while ensuring that the markers 610 do not interfere with surgical tools that may be inserted through the access port 680. The non-uniform structure of the extended arm 682 for the markers 610 enables the tracking system 213 to discern both the position and orientation of the access port 680 in response to instructions corresponding to the tracking software, for example. Likewise, an onboard or associated mobile unit tracking system may allow for self-determination, in some embodiments, of the mobile unit's position/orientation relative to the tracked surgical port and defined surgical site.

Figure 7:
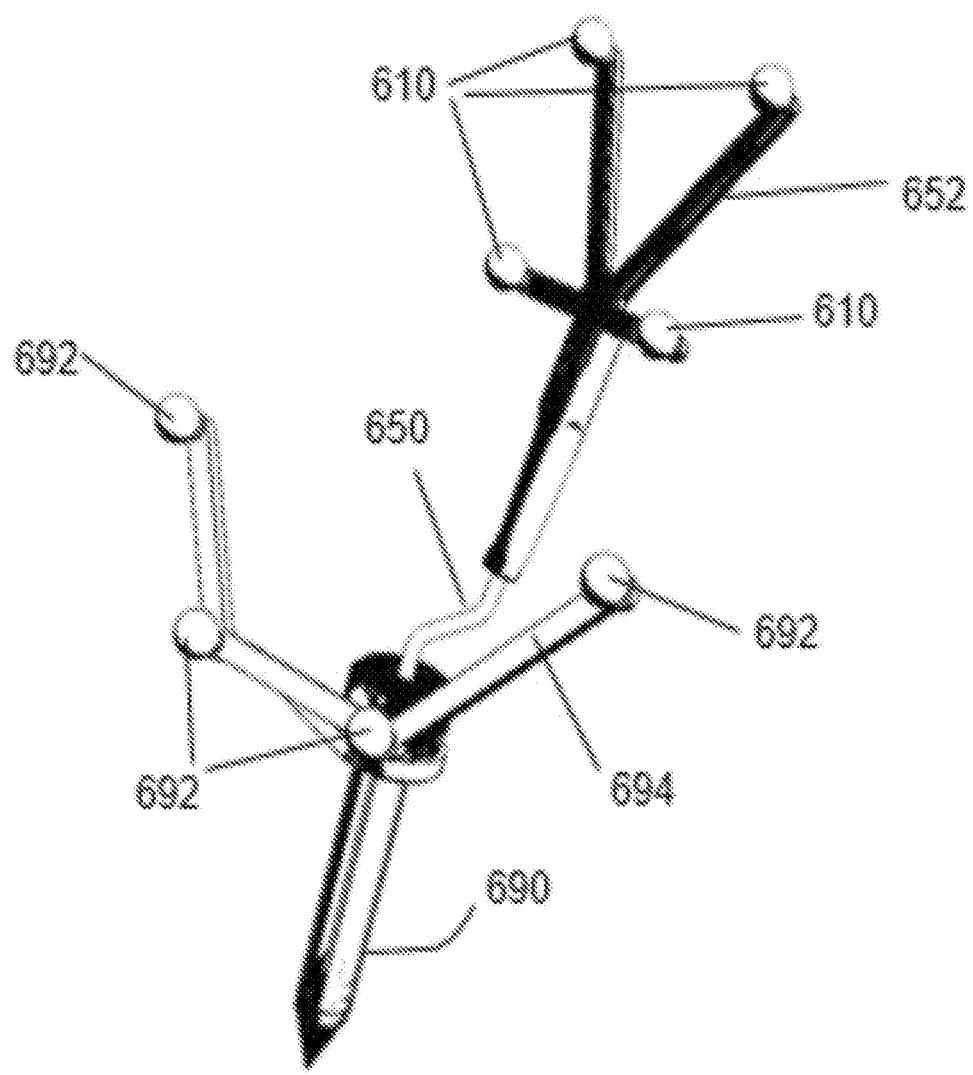
FIG. 7 is a perspective view of the pointing tool of FIG. 6C, engaged with a trackable access port, in accordance with an embodiment of the present disclosure.

With reference to FIG. 7, and in accordance with one embodiment, the tracked tool 603 of FIG. 6C is shown engaged with a tracked access port 690, whereby the tracking markers 610 rigidly associated with the pointing tool 650 via support structure 652 are automatically discernable by the tracking/navigation system from the tracking markers 692 rigidly associated with the access port 690 via distinct support structure 694. Accordingly, the pointing tool 650 and access port 690 are separately trackable by the tracking system 213 of the navigation system 200 (or similar onboard or distributed tracking system as noted above) and are differentiable as unique objects in images rendered on the display device 205.

As noted above, by mapping each instrument's position and orientation, the tracking system may also generally extrapolate a location and orientation of the instrument's various segments, such as an instrument's tip for example, when located and used within the surgical cavity (i.e. down-port location and orientation in the context of a port based procedure). Accordingly, by instrumenting the tip or other segment of a trackable tool, instrumentation-related (sensor) data may also be dynamically associated with the tracked position and orientation of the tool (i.e. tool tip), and effectively mapped in relation thereto even when the tool tip location is obscured to the external viewer/scope. Therefore, a tracked sensored tool, e.g. tool tip, may provide real-time intraoperative visibility otherwise unavailable using pre-operative imaging and intraoperative external scope or camera view angles. Using video and image overlays, as introduced above, tracked tool tip instrumentation may further accentuate available intraoperative data by enhancing real-time data available during the procedure, which is otherwise unavailable using an external scope and cameras.

For example, a tracked sensored tool tip may be enhanced via the disposition of one or more cameras (e.g. miniature camera with a micro lens) at the tool tip to provide real-time intraoperative inner-cavity or down-port (within the context of a port-based procedure) images. For example, such down-port or inner-cavity real-time visible intraoperative imaging may allow for the real-time capture of otherwise obscured or challenging inner-cavity views.

Alternatively, or in combination therewith, the tracked tool tip may be sensored with one or more sensors (e.g. micro-sensors) such as a pressure sensor or the like to capture distinct or further inner-cavity or down-port characterizations otherwise unavailable. For example, a tracked displaceable down-port or inner-cavity pressure sensor may allow for the effective location of an obscured bleeding site, for example, which can then be more effectively addressed (e.g. via bipolar or other method) as compared to current methods, which generally require a blind or mostly obscured visual extra-cavity assessment.

With particular reference back to FIG. 4, and in accordance with one embodiment, the mobile imaging sensor and display unit 505 illustratively comprises a rigid tracking portion, such as tracking marker tree 510 encompassing a set of configurationally and recognizably predisposed tracking markers 512 (i.e. fiducial markers), such as those previously discussed with respect to the examples of FIGS. 6A to 6D. For instance, the tool's tracking marker tree 510 may include a set of tracking markers 512 rigidly mounted in a distinctly recognizable geometric configuration via a designated support structure (e.g. a unit-specific marker configuration and/or type for automated tool type recognition and comprehensive real-time tracking and image display alignment, overlay, annotation and/or A/R capabilities). The various tracking techniques, marker types and configurations described above are equally applicable in this example.

The unit may consist of a dedicated application-specific unit, for example, conceived and manufactured for this intended purpose, or again comprise or be adapted from a conventional mobile camera-enabled display unit, such as a tablet, camera-enabled smart phone, phablet, or like computing device generally known in the art. For example, a conventional mobile computing device may combine sufficient image processing and rendering capabilities with available mobile communication resources and interfaces (e.g. Wi-Fi, Bluetooth, etc.), user interfaces (e.g. touchscreen, wired or wireless input/output interfaces, and/or voice recognition and/or controls, etc.) and image capture capabilities to deliver at least some of the features and functions described herein, while optionally also leveraging one or more device customizations to provide greater usability and versatility within the surgical environment particularly considered herein. For example, resident image magnification capabilities of the standard tablet or smartphone device may not be sufficient to address the surgical site requirements of certain surgical procedures, and may thus require external enhancements (e.g. external optical attachments and/or components) to provide adequate image magnification. Likewise, in the context of spectrally-specific imaging, external light sources such as IR, UV or wavelength specific light sources (e.g. laser, LED, etc.) and corresponding optical sensors may be provided on a patient-facing side of the device (i.e. opposite the device display screen 564) and directly and/or indirectly communicatively linked to the processing resources of the unit 505 or navigation system 200 as a whole (e.g. via Wi-Fi or Bluetooth, or again via a direct wired or cabled (e.g. USB) connection to the device). In the illustrated embodiment, a fixedly disposable unit shell or holder (not shown) may encompass some of these add-on capabilities, and further include attachment or integration of the unit tracking marker tree 510 or similar tracking features.

Alternatively, a customized mobile device may be manufactured to integrate the various optical, electronic, communication and processing resources required to interface with the surgical navigation and/or tracking systems and provide the deliver the trackable image sensing and display functions described herein. Various hybrid manufactures, adaptations, optimizations and configurations may also be considered, as will be readily appreciated by the skilled artisan.

As noted above, the unit 505 is amenable for operative or integral coupling to a manually or robotically articulated arm coupler, grip or clasp, as the case may be, whereas tracking portion 1510 is shaped and oriented relative to the unit body so to remain visible to the tracking system (i.e. optical tracking system 213 of FIG. 2). These and other tracking portion configurations, as illustrated for example in FIGS. 6A-6D, may be considered, as will be readily appreciated by the skilled artisan.

Figure 5B:
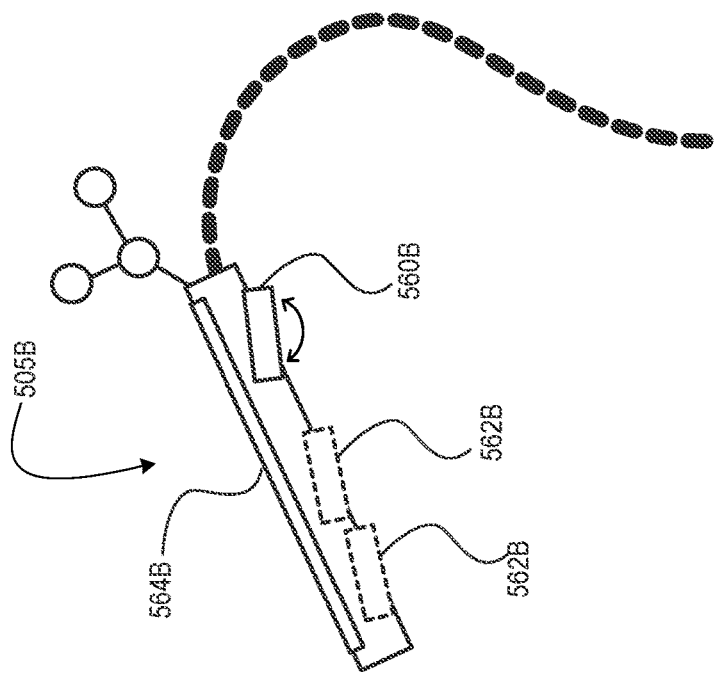
FIGS. 5A and 5B are schematic diagrams of an adjustable trackable mobile imaging sensor and display unit, in accordance with different embodiments of the present disclosure.
Figure 5A:
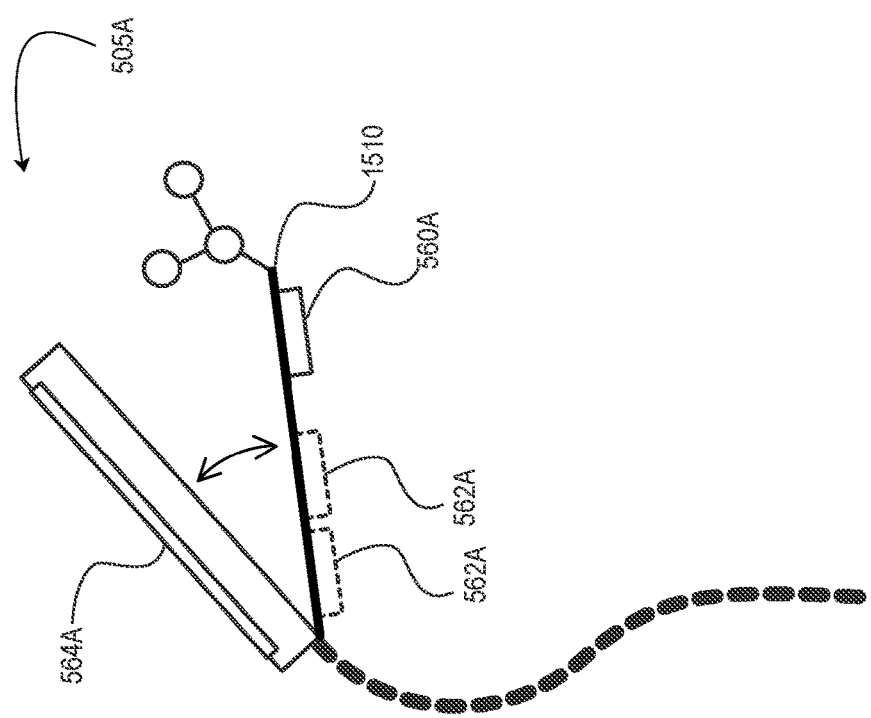

With reference to FIGS. 5A and 5B, alternative mobile unit designs and configurations are shown as mobile units 505A and 505B, respectively, where similar reference numerals are used herein to identify similar unit components. In these particular embodiments, units 505A and 505B are configured to provide adjustable imaging sensors and/or probes (560A, 560B, 562A, 562B) in that a sensor/probe (optical) line-of-sight axis may be adjusted at an angle relative to a unit display (564A, 564B), particularly where a direct line-of-sight imaging sensor/probe and display configuration is not convenient or ergonomically ideal given the application at hand. For example, it may be that the surgeon, while benefiting from the near line-of-sight configuration made available by the mobile unit, would prefer to adjust an angle of the display relative to the imaging sensor(s)/probe(s), an orientation of the latter generally dictated by the surgical procedure and environment and remaining static throughout such procedure in some examples. This may thus allow the surgeon to maintain near line-of-sight visibility on the unit's display screen without imposing certain ergonomic discomforts that may otherwise be imposed by a non-adjustable unit. As noted above, various touchscreen, remote input and/or voice-activated controls may be leveraged to make such adjustments.

With particular reference to FIG. 5A, the mobile unit 505A comprises a pivoting housing 574A allowing for the mobile display 564A to pivot relative to the unit's imaging sensor(s)/probe(s) 560A (562A). With reference to FIG. 5B, the mobile unit 505B rather comprises articulated sensor(s)/probe(s) 560B (562B) that can be dynamically articulated, e.g. via a resident motorized control (not shown), so to dynamically adjust a image sensing and/or probing angle of the unit relative to the display screen 564B. As will be appreciated by the skilled artisan, different sensor/probe adjustment and/or alignment mechanisms may be considered within the present context to provide a similar effect, and that, without departing from the general scope and nature of the present disclosure.

With continued reference to FIG. 4, an illustrative control and processing unit 430 is provided, which may consist of a standalone or subcomponent of an overall surgical system processing and control unit, and which may be resident on, partially distributed on or from, or remotely operated from the processing resources of the mobile unit 505. For example, in some embodiments, the computation resources of the mobile unit 505 may be limited to the capture and display of images, with the bulk of image processing being relegated to a central control and processing unit by way of wired and/or wireless communications, e.g. where raw and processed image data is transferred between from and to the mobile unit 505 for display. In other embodiments, computational resources of the mobile unit 505, e.g. as common to most modern tablets or smartphones, may be leveraged to execute the bulk of imaging processing, whereby pre-operative, external intraoperative and/or other A/R or like overlay data may be communicated to the mobile unit 505 for concurrent processing with real-time image capture. In such embodiments, location tracking may also be at least in part executed by the mobile unit 505, for example, as a function of an externally tracked mobile unit location and/or as a function of the mobile unit's own location tracking, e.g. by way of mobile unit inertial motion sensor tracking and/or relative position tracking based on a surgical site marker(s) or the like.

In general, the control and processing unit 430, be it resident, distributed or external to the mobile unit 505, may include, but is not limited to comprising one or more processors 432 (for example, a CPU/microprocessor or a graphical processing unit, or a combination of a central processing unit or graphical processing unit), bus 444, memory 434, which may include random access memory (RAM) and/or read only memory (ROM), one or more internal storage devices 446 (e.g. a hard disk drive, compact disk drive or internal flash memory), a power supply 448, one more communications interfaces 428, optional external storage 450, display image/data processing 438, and one or more input/output devices and/or interfaces 427. For example, I/O devices and/or interfaces 427 may include, but are note limited to, a wireless receiver/transmitter and antenna 426, a display (i.e. mobile unit display 564, and optionally one or more of displays 205, 211 of FIG. 2 and/or a linked graphical user interface (GUI) or the like), one or more imaging sensors, such as mobile unit imaging sensor(s) 560, 562 (e.g. such as those used in a digital still camera or digital video camera, and/or complementary imaging sensors such as IR, UV, broad or narrow spectrum sensors, spectrometers, optically filtered sensors, etc.). Other I/O devices and/or interfaces may optionally include, but are not limited to, a speaker, a clock, an output port, a user input device, such as a keyboard, a keypad, a mouse, a position tracked stylus, a foot switch, and/or a microphone for capturing speech commands, or the like.

Control and processing unit 430 may be programmed with programs, subroutines, applications or modules, which include executable instructions, which when executed by the processor, causes the system to perform one or more methods described in the disclosure. Such instructions may be stored, for example, in memory 434 and/or internal storage 446. In particular, in the exemplary embodiment shown, image processing module 438 includes computer executable instructions for analyzing captured mobile unit image sensor data (images and/or optical readings) in conjunction with tracking system data and optional complementary pre-operative and/or intraoperative data. For example, computer readable instructions may be provided for processing captured image sensor data in order to not only render a (magnified) line-of-sight or near line-of-sight imaging of the surgical site to the surgeon, but also provide useful pre-operative, intraoperative, and/or A/R overlays/integrations positionally aligned therewith on the basis of mobile unit positional tracking and image capture parameters, for example. For example, the image processing module 438 may be used to align and/or overlay pre- and intraoperative data in the form of complementary flat or 3D images, overlays, annotations and/or A/R displays to relay perfusion maps, DTI, angiographies, MiII, CT, OCT, fluorescence or different white light data, properties and/or images. Other complementary or A/R data may include, but is not limited to, pre-operative or intraoperative surgical planning and/or navigation data, surgical annotations or markers, operating and/or imaging parameters, magnification data, tracking data, etc.

The image processing module 438 may also allow for the capture, storage and/or display of different image views and/or perspectives, such as, but not limited to, different magnifications (micro, macro, zoom, etc.), preset A/R modes, illumination and display modes (e.g. white light, IR, UV, overlay, filtered, etc.), or the like.

As noted above, the spatial location/orientation of the mobile unit relative to the surgical site may be correlated with the recorded imaging data via the tracking data gathered and processed by the illustrated tracking and navigation module 436. For example, the tracking and navigation module 436 may include executable instructions for processing tracking data, and/or for rendering a navigation user interface on a display, as discussed above, based on either or both of mobile unit tracking 452 and/or surgical tool (e.g. access port surgical site pointing or locating tool) tracking 454, for example.

Although only one of each unit component is illustrated in FIG. 4, any number of each component can be included in the control and processing unit 430. For example, a computer typically contains a number of different data storage media. Furthermore, although bus 444 is depicted as a single connection between all of the components, it will be appreciated that the bus 444 may represent one or more circuits, devices or communication channels which link two or more of the components. For example, in personal computers, bus 444 often includes or is a motherboard. Control and processing unit 430 may include many more or less components than those shown. It is also noted that one or more external subsystems, such as a tool tip sensor data processing device, may be distinctly implemented and communicatively linked to an overall surgical system control and processing unit, or form an integral part thereof.

In one embodiment, control and processing unit 430 may be, or include, a general purpose computer or any other hardware equivalents, such as a mobile computing device including optionally, a mobile computing device adapted for use as mobile unit 505. Control and processing unit 430 may also be implemented as one or more physical devices that are coupled to processor 432 through one of more communications channels or interfaces. For example, control and processing unit 430 can be implemented using application specific integrated circuits (ASICs). Alternatively, control and processing unit 430 can be implemented as a combination of hardware and software, where the software is loaded into the processor from the memory or over a network connection.

Figure 8:
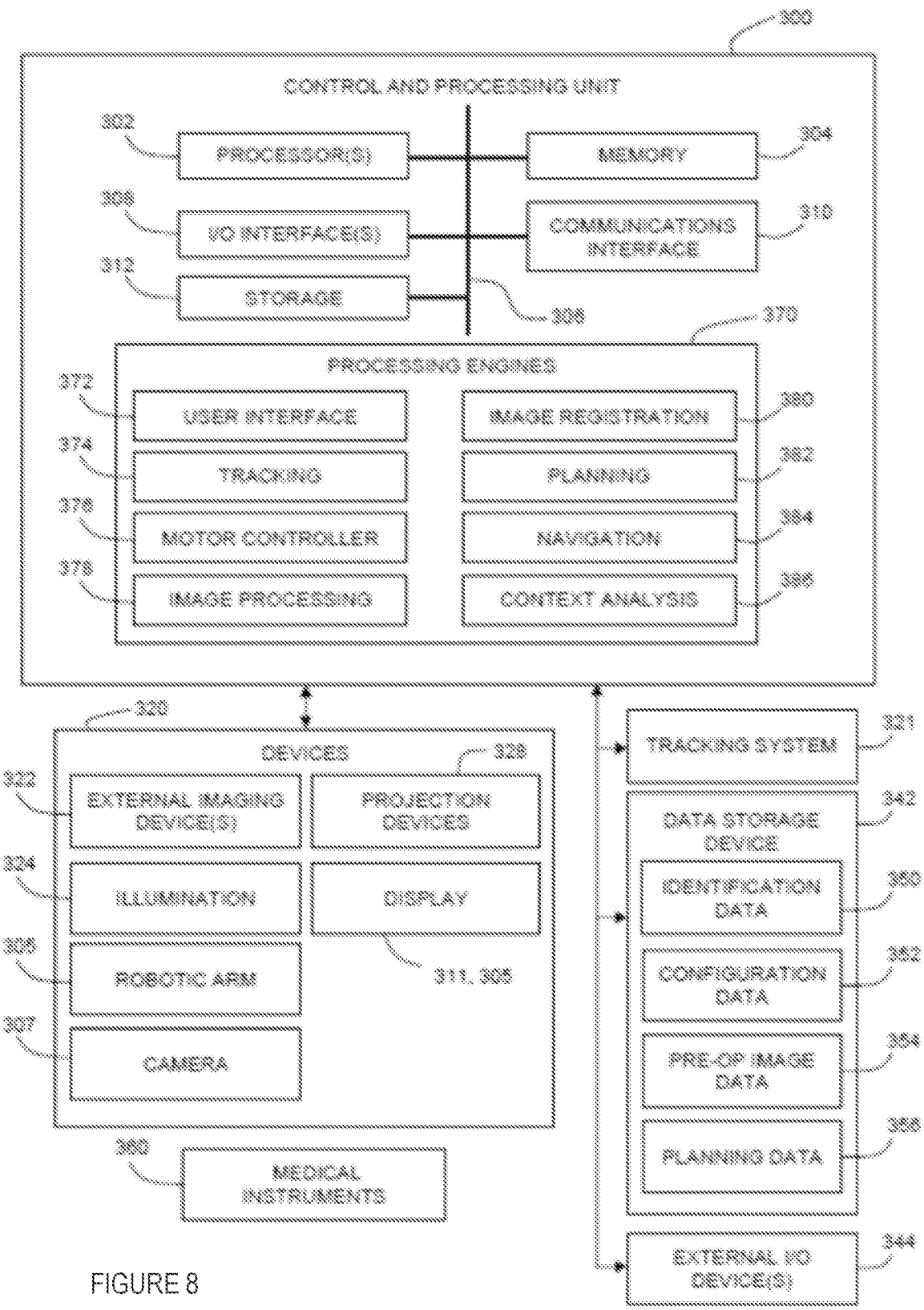
FIG. 8 is a schematic diagram illustrating an exemplary relationship between components of a surgical navigation system, such as a control and processing unit, a tracking system, a data storage device for the tracking system, system devices, and medical instruments/tools, in accordance with an embodiment of the present disclosure.

With reference to FIG. 8, and in accordance with one embodiment, relationships between components of an overall surgical navigation system 200, such as a control and processing unit 300, a tracking system 213, a data storage device 342 for the tracking system 213, and system devices 320, and medical instruments 360, will now be described. The control and processing unit 300 comprises at least one processor 302, a memory 304, such as a non-transitory memory device, a system bus 306, at least one input/output interface 308, a communications interface 310, and storage device 312. The control and processing unit 300, which may encompass or interface with control and processing unit 430 of FIG. 4, is interfaced with other external devices, such as the tracking system 213, data storage 342 for the tracking system 213, and external user input and output devices 344, optionally comprising, for example, at least one of a display device, such as mobile unit display 564 and optional display devices 211, 205, a keyboard, a mouse, a foot pedal, a microphone, and a speaker.

The data storage 342 comprises any suitable data storage device, such as a local or remote computing device, e.g. a computer, hard drive, digital media device, or server, having a database stored thereon. The data storage device 342 includes identification data 350 for identifying at least one medical instrument 360 (e.g. such as mobile unit 505 and/or related surgical tools or equipment) and configuration data 352 for associating customized configuration parameters with at least one medical instrument 360. The data storage device 342 further comprises at least one of preoperative image data 354 and medical procedure planning data 356. Although data storage device 342 is shown as a single device, it will be understood that, in other embodiments, the data storage device 342 may comprise multiple storage devices. The data storage device 342 is also configured to store data in a custom data structure corresponding to various 3D volumes at different resolutions, wherein each may be captured with a unique time-stamp and/or quality metric. This custom data structure provides the system 200 (FIGS. 1 and 2) with an ability to move through contrast, scale, and time during the surgical procedure.

Medical instruments (tools) 360 are identifiable by the control and processing unit 300, wherein the medical instruments 360 are coupled with, and controlled by, the control and processing unit 300. Alternatively, the medical instruments 360 are operable or otherwise independently employable without the control and processing unit 300. The tracking system 213 may be employed to track at least one of the medical instruments 360 and spatially register the at least one medical instrument 360 in relation to an intraoperative reference frame. As noted above, the tracking system 213 may thus furnish the requisite position, orientation and location data to associate sensed tool data with corresponding locations within the surgical cavity.

The control and processing unit 300 is also interfaceable with a number of configurable devices, and may intraoperatively reconfigure at least one such device based on configuration parameters obtained from configuration data 352. Examples of devices 320 include, but are not limited to, at least one external imaging device 322 (e.g. image sensors 560, 562 of mobile unit 505 shown in FIG. 3), at least one illumination device 324 (e.g. again optionally forming part of mobile unit 505), a robotic arm 202 (i.e. as appropriate to provide precision displacement of surgical tools and/or equipment), an optional projection device 328 (e.g. to concurrently render captured images on a complementary or duplicate display 205, 211), and at least one display device, such as display devices 564 of mobile unit 505.

The control and processing unit 300 is operable by the at least one processor 302 and the at least one memory 304. For example, the functionalities described herein are at least partially implemented via hardware logic in processor 302 by way of the instructions stored in memory 304 though at least one processing engine 370. Examples of processing engines 370 include, but are not limited to, user interface engine 372, tracking engine 374, motor controller 376, image processing engine 378, image registration engine 380, procedure planning engine 382, navigation engine 384, and context analysis module 386. Understood is that the system 200 (FIGS. 1 and 2) is not intended to be limited to the components shown in the several figures of the Drawing. One or more components of the control and processing 300 may be provided as an external component or device. In one alternative embodiment, navigation module 384 may be provided as an external navigation system that is integrated with control and processing unit 300.

Embodiments of the system 200 of FIG. 2 may be implemented using processor 302 without additional instructions stored in memory 304. Embodiments may also be implemented using the instructions stored in the memory 304 for execution by one or more general purpose microprocessors.

Thus, the disclosure is not limited to a specific configuration of hardware, firmware, and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The preceding exemplary embodiments involve systems and methods in which a mobile imaging sensor and display unit is intraoperatively configured based on the identification of the unit's relative position/orientation to the surgical site. In some embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids (e.g. wash fluids) during the medical procedure, and may further identify the type of fluid. Each of these examples relate to the image-based identification of information pertaining to the context of the medical procedure.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the Internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Figure 9:
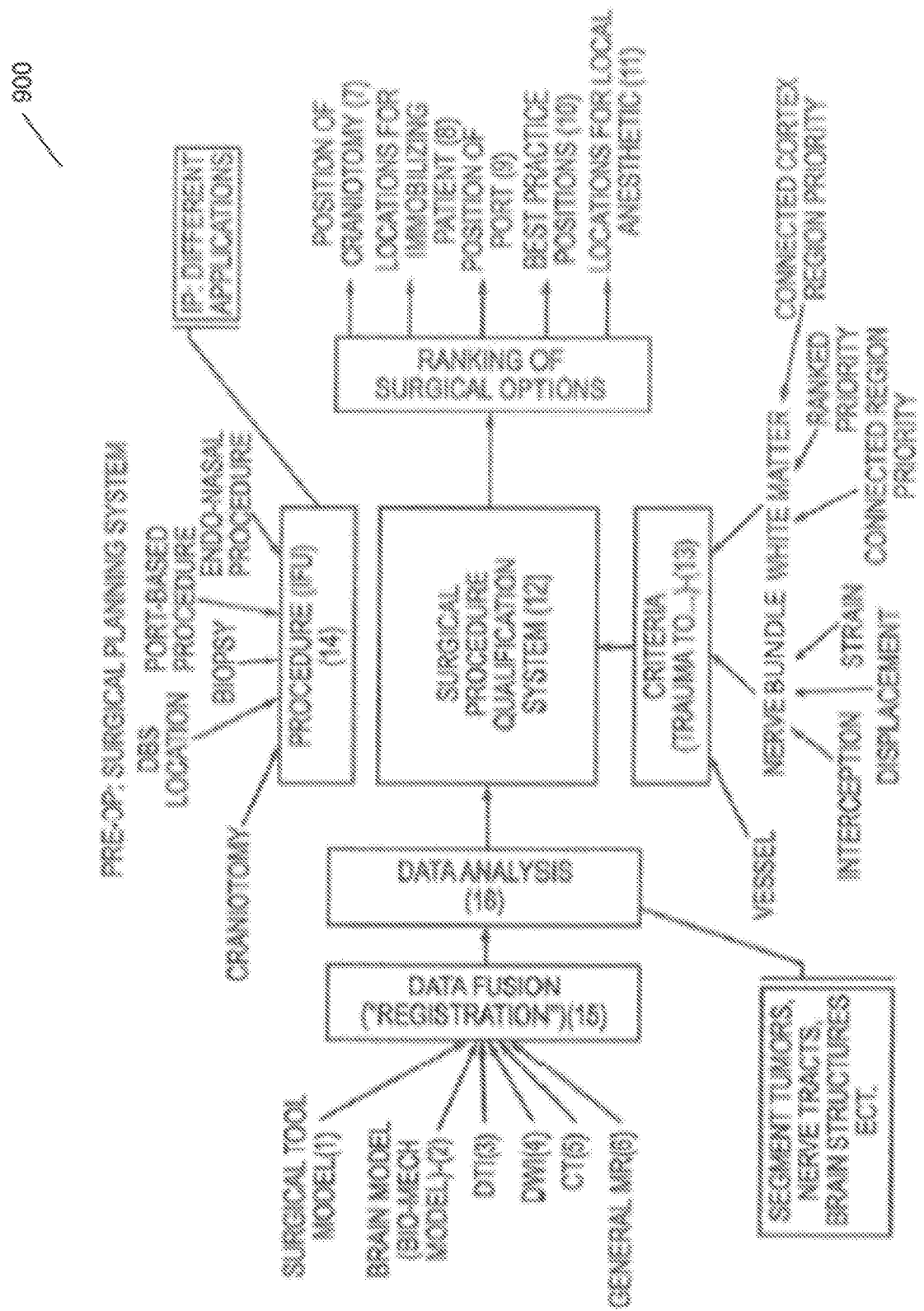
FIG. 9 is a schematic diagram illustrating a pre-operative surgical planning system for use with a medical navigation system, in accordance with an embodiment of the present disclosure.

With reference to FIG. 9, a schematic diagram is provided to illustrate a pre-operative surgical planning system 900 for use with a navigation system 200, in accordance with an embodiment of the present disclosure. The pre-operative surgical planning system 900 comprises components and inputs for planning and scoring surgical paths.

Figure 10:
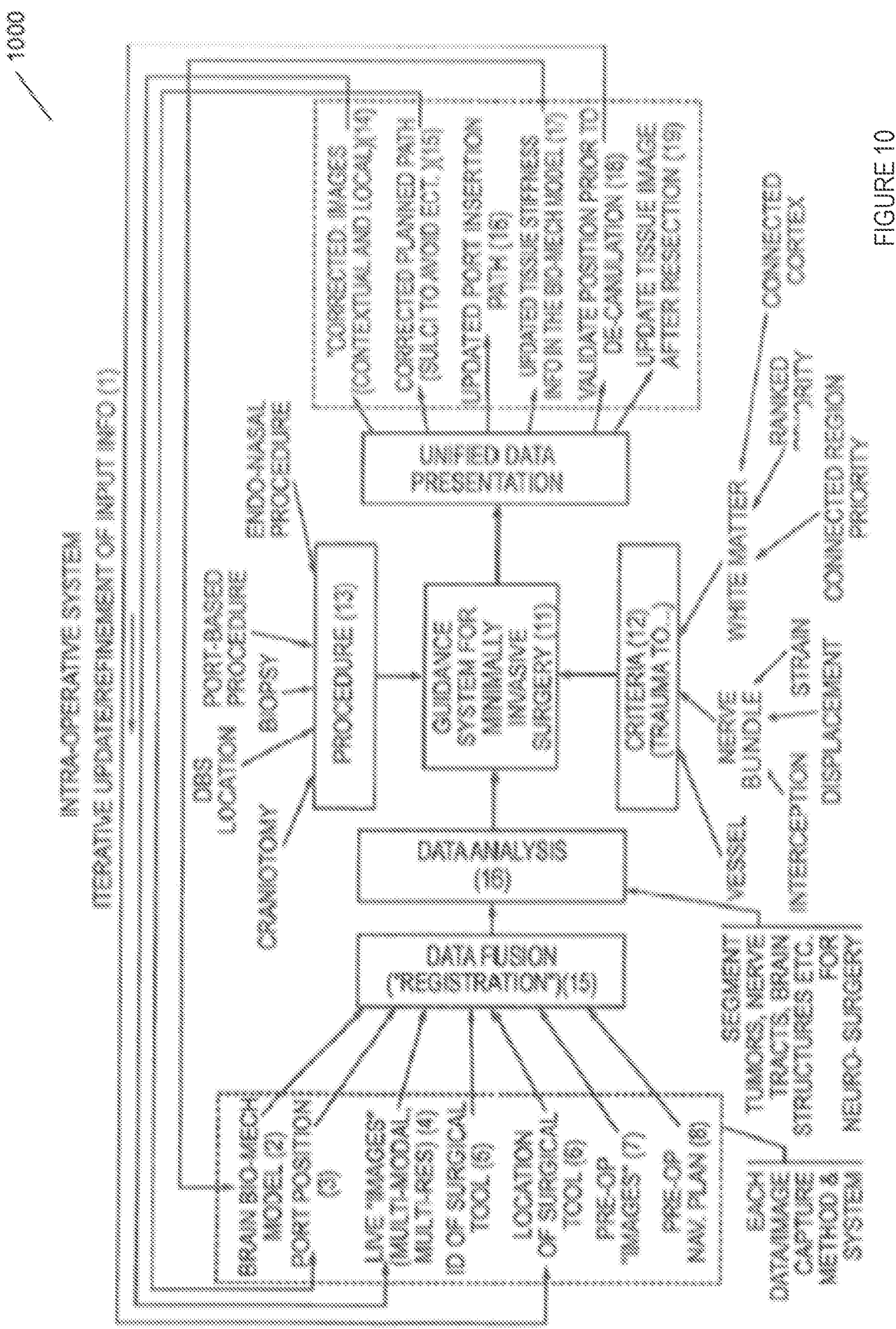
FIG. 10 is a schematic diagram illustrating an intraoperative surgical management system for use with a medical navigation system, in accordance with an embodiment of the present disclosure.

With reference to FIG. 10, a schematic diagram is provided to illustrate an intraoperative surgical management system 1000 for use with a navigation system 200, in accordance with an embodiment of the present disclosure. The intraoperative surgical management system 1000 comprises components and inputs for navigation along the surgical paths produced by the pre-operative surgical planning system 900, as shown in FIG. 9. The intra-operative surgical management system 1000 can be used as a surgical planning and navigation tool in the pre-operative and intra-operative stages. Data input(s) of the surgical planning steps and surgical procedures, as shown in FIG. 9, can be used as input(s) to the intraoperative navigation stage performable by the intraoperative surgical management system 1000.

The intraoperative surgical management system 1000 of the navigation system 200 provides a user, such as a surgeon, with a unified technique for navigating through a surgical region by utilizing pre-operative data input(s) and updated intraoperative data input(s), e.g. as provide by the mobile imaging sensor and display unit and/or related intraoperative instruments/tools. The processor(s), such as the at least one processor 302, is operable by way of a set of instructions and/or algorithms storable in relation to a non-transitory memory device, such as the at least one memory 304, wherein the at least one processor 302 is configured to: analyze pre-operative data input(s) and intraoperative data input(s) and update surgical plans during the course of surgery accordingly.

For example, if intraoperative input(s) in the form of newly acquired images identified a previously unknown or unidentified nerve bundle or a previously unknown or unidentified fiber track, the at least one processor 302 can use these intra-operative input(s), if desired, for updating the surgical plan during surgery to avoid contacting the nerve bundle. The intraoperative input(s) may include a variety of input(s), including local data gathered using a variety of sensor(s), such as at least one intraoperative imaging sensor, e.g. as provide by mobile unit 505. In some embodiments, the intraoperative surgical management system 1000 of the navigation system 200 may provide continuously updated, e.g., in real-time, intraoperative input(s) in the context of a specific surgical procedure by way of the at least one intraoperative imaging sensor to: validate tissue position, update tissue imaging after tumor resection, and update surgical device position during surgery.

With continued reference to FIG. 10, the intraoperative surgical management system 1000 of the navigation system 200 may provide for re-formatting of the image, for example, to warn of possible puncture of, or collision with, critical tissue structures with a surgical tool during surgery. In addition, the intraoperative surgical management system 1000 may provide imaging and input updates for any shifts or surgical errors that might occur from a needle deflection, tissue deflection, or patient movement as well as provide analysis and transformation of data to correct for imaging distortions, e.g., in real-time. The magnitude of these combined shifts or surgical errors is clinically significant and may regularly exceed 2 cm. Some of the most significant distortions are magnetic resonance imaging (Mill) based distortions such as gradient non-linearity, susceptibility shifts, and eddy current artifacts, which may exceed 1 cm on standard Mill scanners (1.5 T and 3.0 T systems). The intraoperative surgical management system 1000 mitigates, and may eliminate, these combined shifts or surgical errors.

In accordance with some embodiments of the present disclosure, by using the a intraoperative surgical management system 1000, a variety of intraoperative imaging techniques may be implemented to generate intraoperative input(s) by way of a variety of imaging devices, including anatomy specific MM devices, surface array Mill scans, endo-nasal MRI devices, anatomy specific ultrasound (US) scans, endo-nasal US scans, anatomy specific computerized tomography (CT) or positron emission tomography (PET) scans, port-based or probe based photo-acoustic imaging, sensored tool imaging and/or characterization, as well as optical imaging done with remote scanning, or probe based scanning, whereby multi-modal imaging and data are providable and transformable into useful images and data in real-time. Given the advantageous line-of-sight or near line-of-sight positioning of the mobile unit, as described herein, one or more complimentary imaging devices may be strategically disposed on a patient-facing side of the mobile unit to provide direct and trackable line-of-sight access to the surgical site in a convenient form factor that can be directly or indirectly processed for (interactive) display on the mobile unit in real-time.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A mobile system for conducting a surgical procedure on a surgical site, the system comprising:
    a mobile imaging sensor-and-display unit, the mobile imaging sensor-and-display unit comprising a display device and an image-capture device configured to couple with the display device and to align with the surgical site, the image-capture device comprising an imaging device having an imaging modality for capturing an image of the surgical site and a complementary imaging device having a complementary imaging modality for capturing a complementary image of the surgical site, the complementary imaging modality distinct from the imaging modality, the display device configured to render the image and the complementary image, and the mobile imaging sensor-and-display unit configured to facilitate switching between the image and the complementary image respectively based the imaging modality and the complementary imaging modality;
    a tracking engine configured to automatically track an intraoperative location of the mobile imaging sensor-and-display unit relative to an intraoperative location of the surgical site; and
    an image processing engine configured to associate the intraoperative location of the surgical site with the image based on at least the intraoperative location of the mobile imaging sensor-and-display unit.

2. The mobile system of claim 1, further comprising a digital data storage medium configured to store complementary location-specific surgical data, wherein the image processing engine is further configured to associate the complementary location-specific surgical data with the image based on at least the intraoperative location of the surgical site therewith associated.

3. The mobile system of claim 2,
    wherein the complementary location-specific surgical data comprises location-specific pre-operative imaging data, and
    wherein the image processing engine is further configured to instruct the mobile imaging sensor-and-display unit to concurrently render the location-specific pre-operative imaging data with the image on the display screen device.

4. The mobile system of claim 1,
    wherein the tracking engine is further configured to track an intraoperative location of a surgical instrument relative to the intraoperative location of the surgical site, and
    wherein the image processing engine is further configured to concurrently render complementary intraoperative data associated with the surgical instrument with the image on the display device based on at least the intraoperative location of the surgical instrument and the intraoperative location of the surgical site.

5. The mobile system of claim 1, wherein at least one of the image processing engine and the tracking engine is at least partially implemented by a processor of the mobile imaging sensor-and-display unit.

6. The mobile system of claim 1,
    wherein the mobile imaging sensor-and-display unit further comprises a tracking marker, and
    wherein the tracking engine comprises a tracking sensor fixedly disposable at a distance from the mobile imaging sensor-and-display unit for sensing the tracking marker to derive the intraoperative location of the mobile imaging sensor-and-display unit.

7. The mobile system of claim 6, further comprising a surgical site marker fixedly disposable in relation to the surgical site, wherein the tracking sensor concurrently senses the surgical site marker to derive the intraoperative location of the mobile imaging sensor-and-display unit.

8. The mobile system of claim 1, further comprising a surgical site marker fixedly disposable in relation the surgical site, wherein the tracking engine is at least partially implemented by a processor of the mobile imaging sensor-and-display unit for tracking the surgical site tracking marker to derive the intraoperative location of the mobile imaging sensor-and-display unit.

9. The mobile system of claim 1, wherein the imaging device comprises at least one of: a digital camera, an infrared (IR), ultraviolet (UV), broad spectrum, or narrow spectrum imaging device.

10. The mobile system of claim 1, further comprising at least one of:
    an articulated arm configured to adjust a position of the mobile imaging sensor-and-display unit relative to a position of the surgical site, the articulated arm comprising at least one of a manually actuated arm an electrically actuated arm; and
    a voice-recognition interface configured to receive voice-actuated commands for operating the mobile imaging sensor-and-display unit,
    wherein the display device is adjustably angled relative to the image-capture device.

11. The mobile system of claim 1, wherein the mobile imaging sensor-and-display unit is disposable between an operator and the surgical site to provide one of a line-of-sight and a near-line-of-sight in relation to the display device.

12. A mobile device for use during a surgical procedure on a surgical site, the mobile device comprising:
   a display device;
   an image-capture device configured to couple with the display device and to align with the surgical site, the image-capture device comprising an imaging device having an imaging modality for capturing an image of the surgical site and a complementary imaging device having a complementary imaging modality for capturing a complementary image of the surgical site, the complementary imaging modality distinct from the imaging modality, the display device configured to render the image and the complementary image, and the mobile device configured to facilitate switching between the image and the complementary image respectively based the imaging modality and the complementary imaging modality; and
   a tracking marker fixedly disposable in relation to the image-capture device and trackable by a tracking sensor fixedly disposable at a distance therefrom for sensing the tracking marker to track an intraoperative location of the image-capture device relative to an intraoperative of the surgical site and to associate the intraoperative location of the surgical site with the image based at least on the intraoperative location of the image-capture device relative to the intraoperative location of the surgical site.

13. The mobile device of claim 12, wherein the display is configured to concurrently render complementary location-specific surgical data with the image based at least on the intraoperative location of the surgical site associated with the image, wherein the complementary location-specific surgical data comprises at least one of location-specific pre-operative imaging data and complementary intraoperative data associated with a surgical instrument based on an intraoperative location of the surgical instrument relative to the intraoperative location of the surgical site.

14. The mobile device of claim 12, wherein the tracking marker comprises a set of fiducial markers in a fixed arrangement and configured to couple with the image-capture device for tracking a 3D orientation of the image-capture device.

15. The mobile device of claim 12, further comprising a voice-recognition interface configured to receive voice-actuated commands for operating the mobile device, wherein the display device is adjustably angled relative to the image-capture device.

16. The mobile device of claim 12,
   wherein the complementary imaging device is configured to couple with the display device and to align with the surgical site to capture the complementary image of the surgical site, the complementary image concurrently renderable on the display device,
   wherein the complementary imaging device comprises at least one of at least one illuminator and at least one sensor to acquire the complementary image,
   wherein said complementary imaging device comprises at least one of an IR light source, a UV light source, a broad spectrum light source, a laser light source, an IR sensor, a UV sensor, or a narrow spectrum sensor.

17. A mobile device for use during a surgical procedure on a surgical site, the mobile device comprising:
   a display device;
   an image-capture device configured to couple with the display device and to align with the surgical site, the image-capture device comprising an imaging device having an imaging modality for capturing an image of the surgical site and a complementary imaging device having a complementary imaging modality for capturing a complementary image of the surgical site, the complementary imaging modality distinct from the imaging modality, the display device configured to render the image and the complementary image, and the mobile device configured to facilitate switching between the image and the complementary image respectively based the imaging modality and the complementary imaging modality; and
   a resident tracking engine configured to track an intraoperative location of a marker, fixedly associated with the surgical site, relative to the image-capture device and to associate an intraoperative location of the surgical site with the image based at least on the intraoperative location of the marker relative to the intraoperative location of the surgical site.

18. The mobile device of claim 17, wherein the display device is configured to concurrently render complementary location-specific surgical data with the image based at least on the intraoperative location of the surgical site associated with the image.

19. The mobile device of claim 17, further comprising a voice-recognition interface configured to receive voice-actuated commands for operating the mobile device, wherein the display device is adjustably angled relative to the image-capture device.

20. The device of claim 17,
   wherein the complementary imaging device is configured to couple with the display device and to align with the surgical site to capture the complementary image, and the display device further configured to concurrently render the complementary image, and
   wherein said complementary imaging device comprises at least one of an IR light source, a UV light source, a broad spectrum light source, a laser light source, an IR sensor, a UV sensor, or a narrow spectrum sensor.

* * * * *